US011798249B1

(12) United States Patent
Douglas et al.

(10) Patent No.: US 11,798,249 B1
(45) Date of Patent: *Oct. 24, 2023

(54) USING TANGIBLE TOOLS TO MANIPULATE 3D VIRTUAL OBJECTS

(71) Applicants: Robert Edwin Douglas, Winter Park, FL (US); David Byron Douglas, Winter Park, FL (US); Kathleen Mary Douglas, Winter Park, FL (US)

(72) Inventors: Robert Edwin Douglas, Winter Park, FL (US); David Byron Douglas, Winter Park, FL (US); Kathleen Mary Douglas, Winter Park, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/882,796

(22) Filed: Aug. 8, 2022

Related U.S. Application Data

(63) Continuation of application No. 17/181,757, filed on Feb. 22, 2021, now Pat. No. 11,417,071, which is a continuation-in-part of application No. 17/175,815, filed on Feb. 15, 2021, now Pat. No. 11,094,141, which is a continuation of application No. 16/843,988, filed on Apr. 9, 2020, now Pat. No. 10,964,124, which is a continuation of application No. 16/752,662, filed on Jan. 26, 2020, now Pat. No. 10,657,731, which is a continuation of application No. 15/904,092, filed on Feb. 23, 2018, now Pat. No. 10,586,400.

(51) Int. Cl.
*G06T 19/20* (2011.01)
*G06T 15/08* (2011.01)
*G06T 19/00* (2011.01)

(52) U.S. Cl.
CPC .............. *G06T 19/20* (2013.01); *G06T 15/08* (2013.01); *G06T 19/006* (2013.01); *G06T 2219/004* (2013.01); *G06T 2219/2012* (2013.01); *G06T 2219/2016* (2013.01); *G06T 2219/2021* (2013.01)

(58) Field of Classification Search
None
See application file for complete search history.

(56) References Cited

U.S. PATENT DOCUMENTS

| 11,417,071 B1* | 8/2022 | Douglas | G06F 3/013 |
| 2011/0107270 A1* | 5/2011 | Wang | G16H 20/40 |
| | | | 703/11 |

(Continued)

FOREIGN PATENT DOCUMENTS

| DE | 10355617 A1 * | 7/2005 | ......... G06F 3/04812 |

OTHER PUBLICATIONS

J. J. Aloor, P. S. Sahana, S. Seethal, S. Thomas and M. T. R. Pillai, "Design of VR headset using augmented reality," 2016 International Conference on Electrical, Electronics, and Optimization Techniques (ICEEOT), 2016, pp. 3540-3544, doi: 10.1109/ICEEOT.2016. 7755363 (Year: 2016).*

(Continued)

*Primary Examiner* — James A Thompson

(57) ABSTRACT

Virtual tools are used to manipulate aspects of a three-dimensional medical image volume. The virtual tools are registered with the image volume. Presentation of the image volume is manipulated by an image processor in response to use of the virtual tools. The virtual tools may be used to facilitate analysis of the image volume.

20 Claims, 23 Drawing Sheets

(56) References Cited

U.S. PATENT DOCUMENTS

| | | | | |
|---|---|---|---|---|
| 2013/0230224 A1* | 9/2013 | Claude | ................ | G06T 7/12 |
| | | | | 382/173 |
| 2014/0111544 A1* | 4/2014 | Hammond | ............ | G06T 19/006 |
| | | | | 345/633 |
| 2018/0004915 A1* | 1/2018 | Talbot | ................ | G16H 50/20 |
| 2018/0225993 A1* | 8/2018 | Buras | ................ | A61B 34/20 |
| 2018/0325608 A1* | 11/2018 | Kang | ................ | A61B 17/1671 |
| 2019/0094981 A1* | 3/2019 | Bradski | ............ | H04N 21/414 |
| 2020/0337789 A1* | 10/2020 | Meglan | ............ | G09B 23/28 |
| 2020/0387706 A1* | 12/2020 | Zur | ................ | G06T 15/08 |
| 2021/0169581 A1* | 6/2021 | Calloway | ............ | A61B 34/30 |

OTHER PUBLICATIONS

X. Min, W. Zhang, S. Sun, N. Zhao, S. Tang and Y. Zhuang, "VPModel: High-Fidelity Product Simulation in a Virtual-Physical Environment," in IEEE Transactions on Visualization and Computer Graphics, vol. 25, No. 11, pp. 3083-3093, Nov. 2019, doi: 10.1109/TVCG.2019.2932276 (Year: 2019).*

* cited by examiner

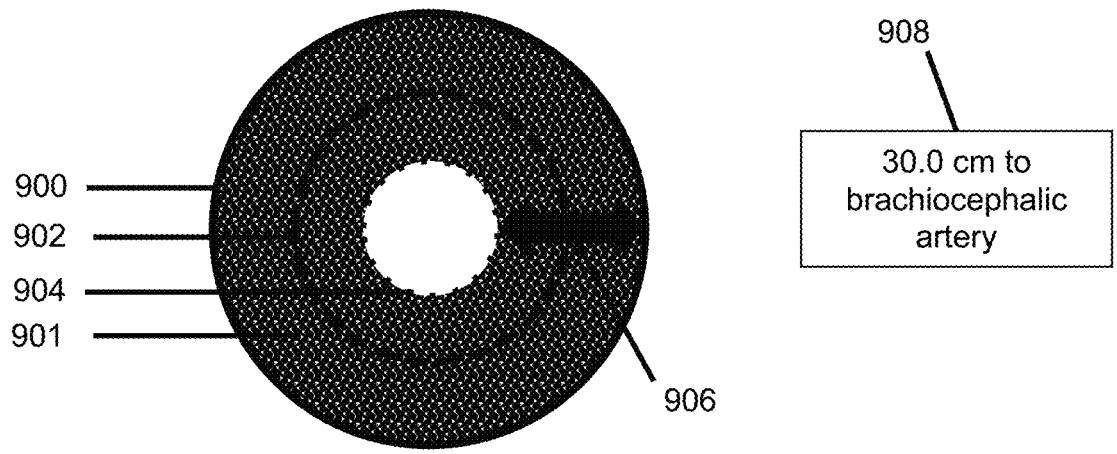
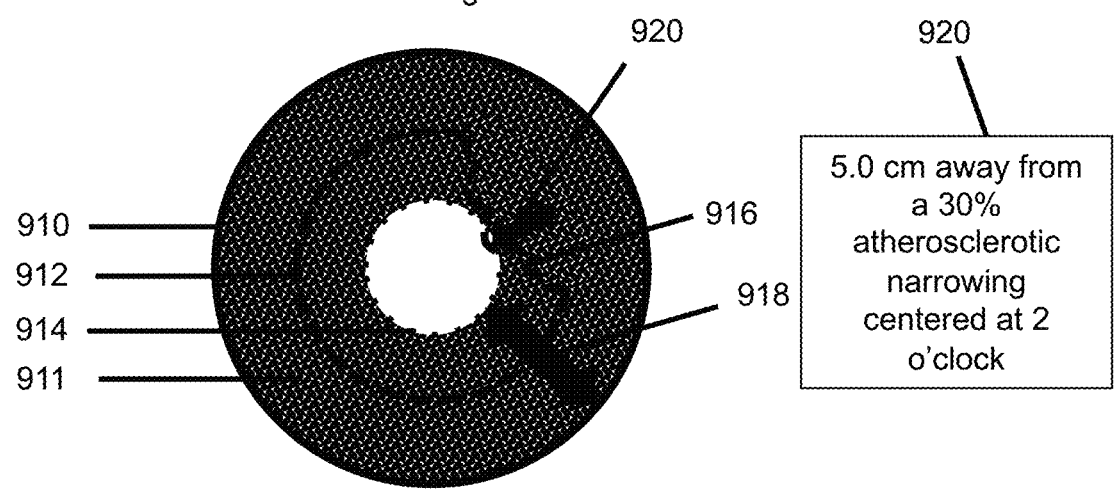
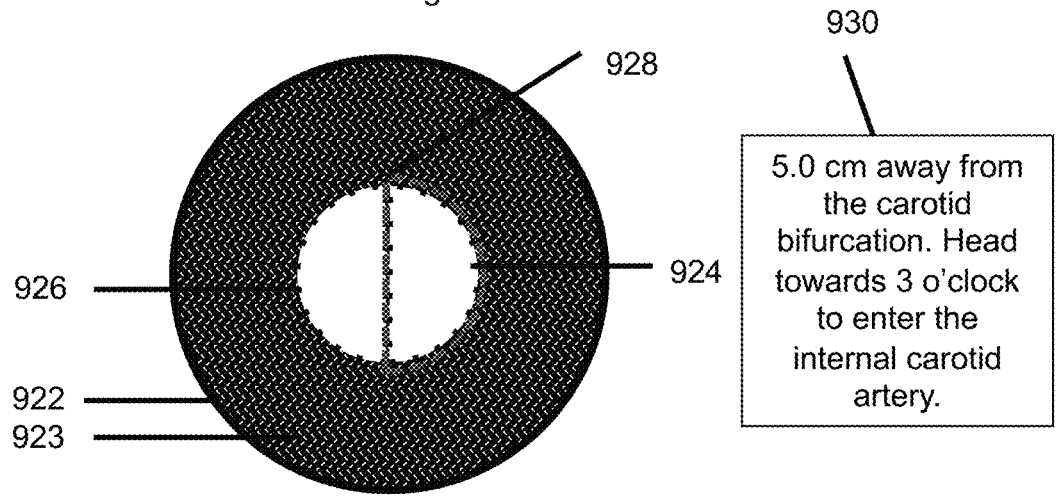

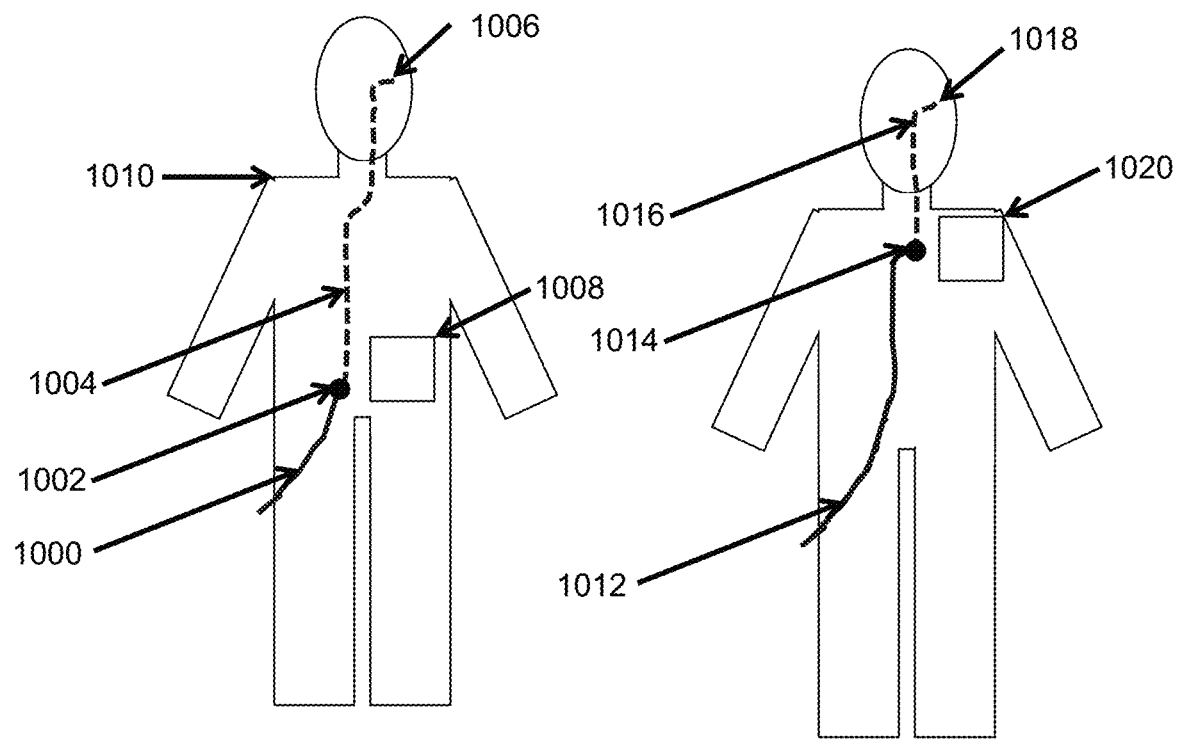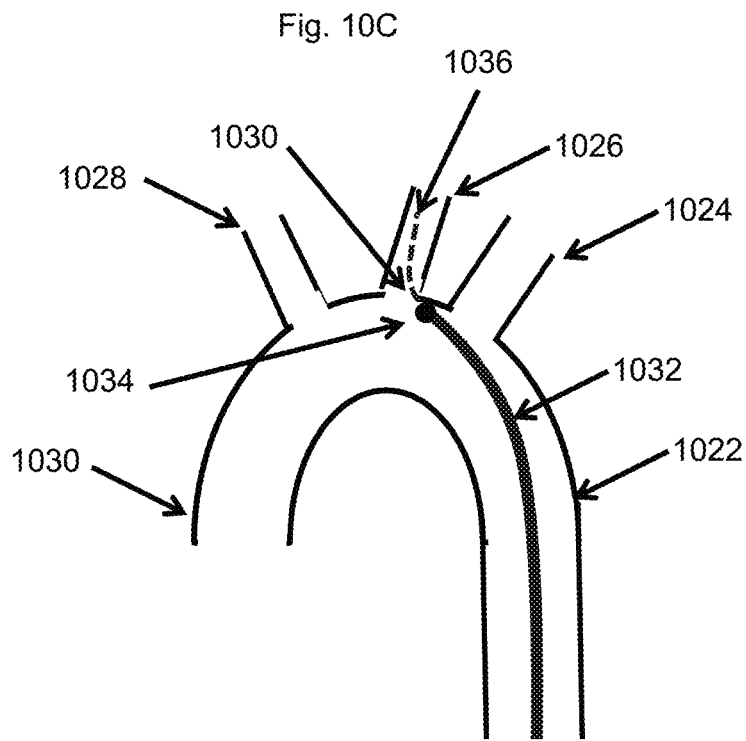

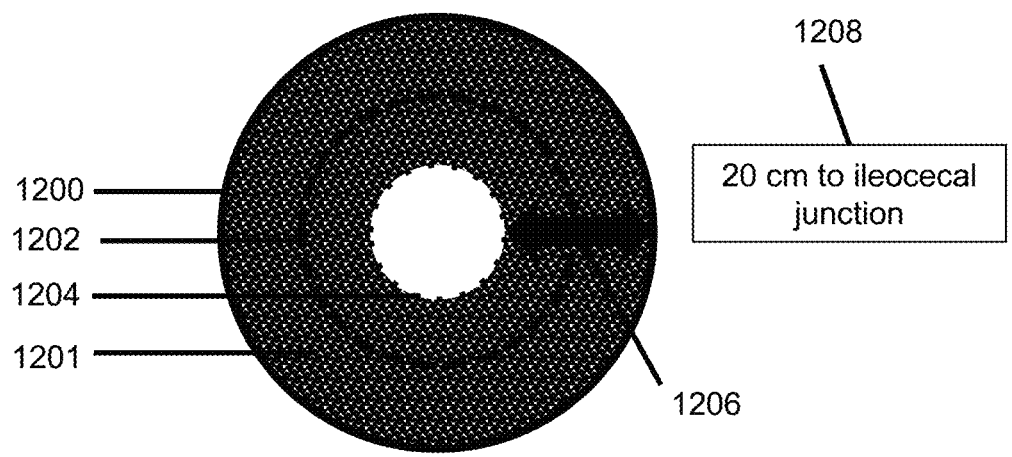
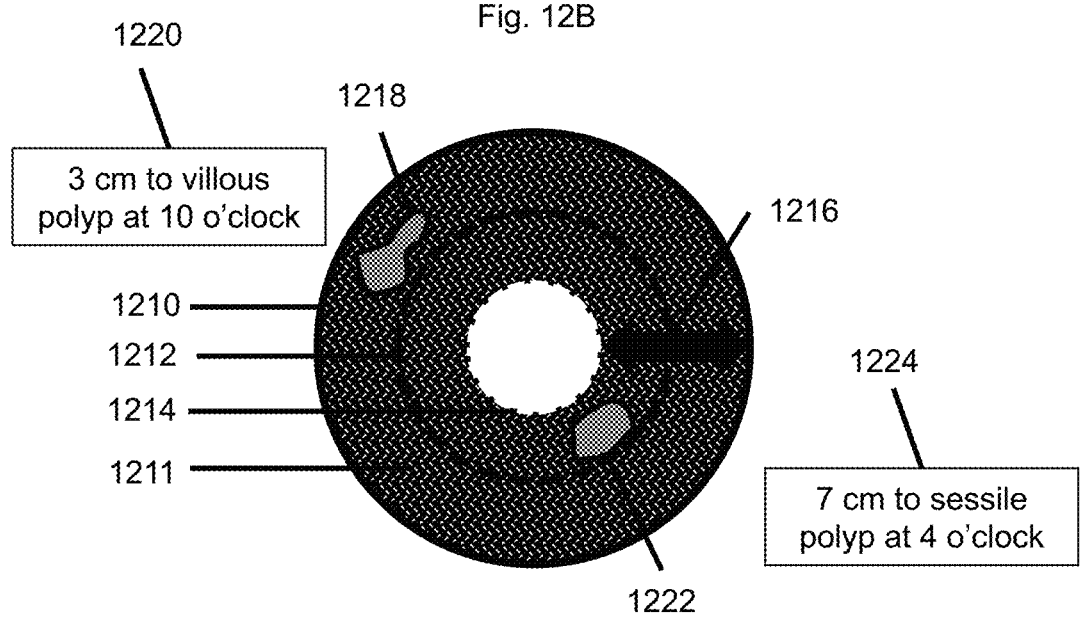

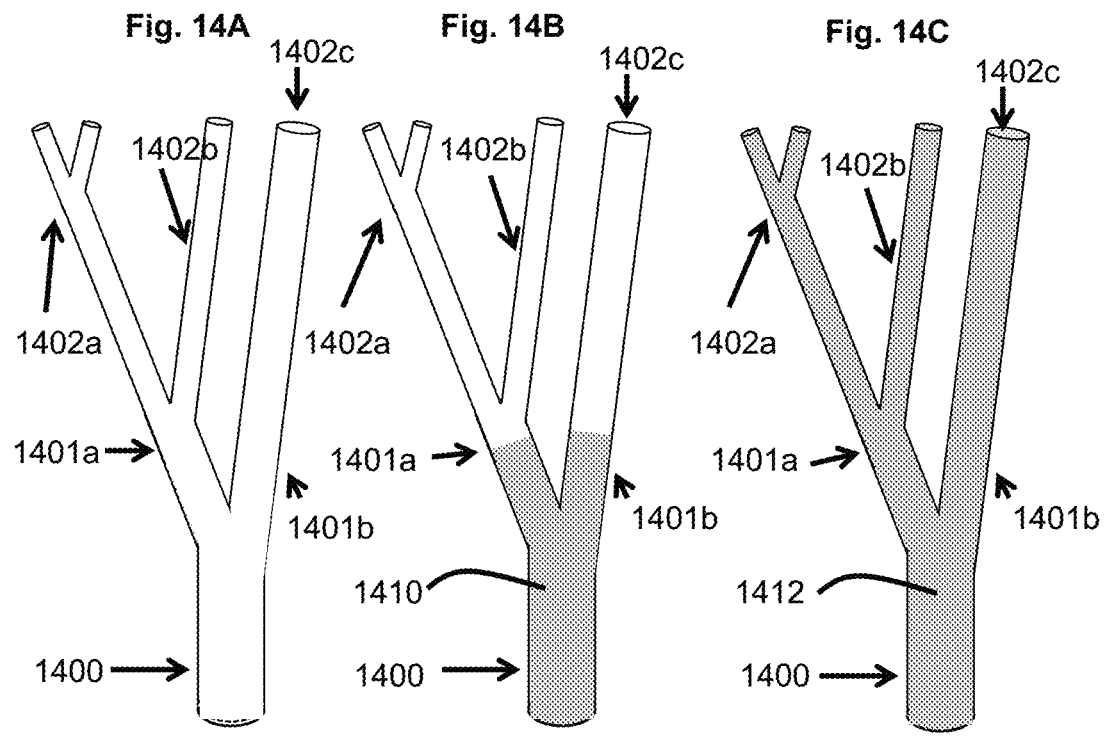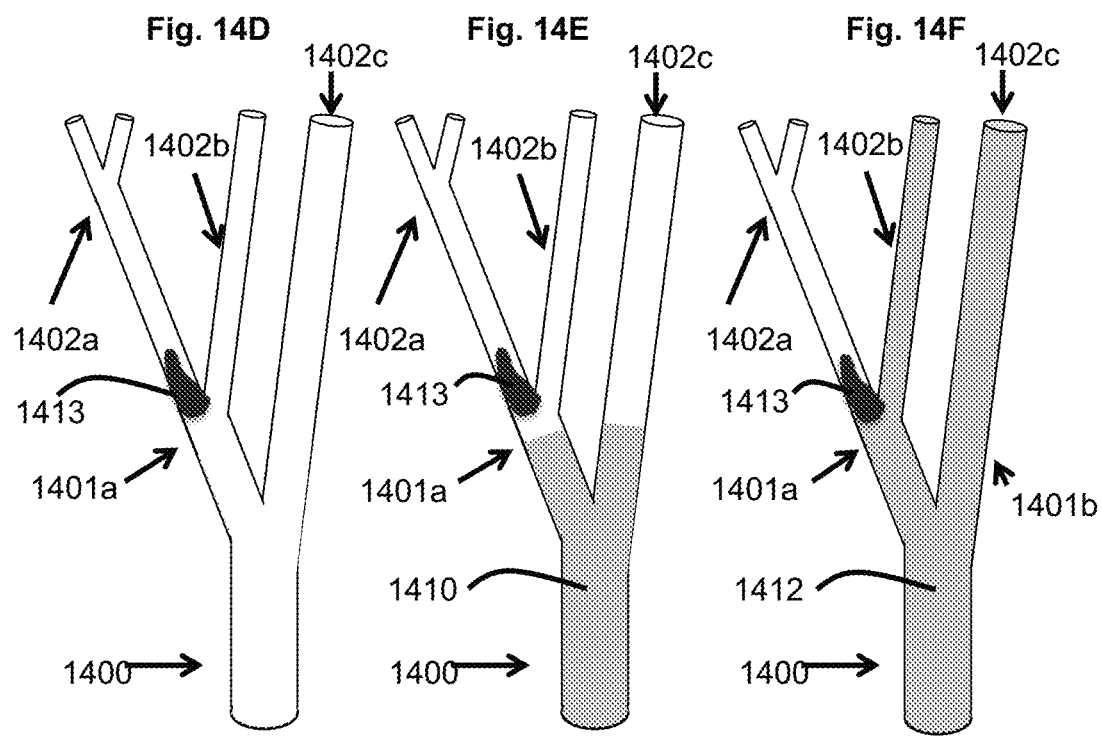

Radiology Report

Exam: CT Abdomen/Pelvis
Technique: 4 phase CT exam of the liver was performed.
History: Please characterize liver mass discovered on ultrasound.
Comparisons: Ultrasound exam from 1 Jan 2018
Findings:
Heart: Unremarkable
Lungs: Unremarkable
Liver: There is a enhancing lesion measuring 3 cm in the non-cirrhotic liver consistent with a focal nodular hyperplasia.
Gallbladder: Unremarkable
Spleen: Unremarkable
Pancreas: Unremarkable
Adrenal glands: Unremarkable
Kidneys: Unremarkable
Ureters: Unremarkable
Bladder: Unremarkable
Gastrointestinal tract: Unremarkable
Vasculature: Unremarkable
Lymph nodes: Unermarkable
Bones: Unremarkable
Soft tissues: Unremarkable Impression:
1. No acute intra-abdominal abnormality.
2. Incidental note of a benign focal nodular hyperplasia in the liver.

2300

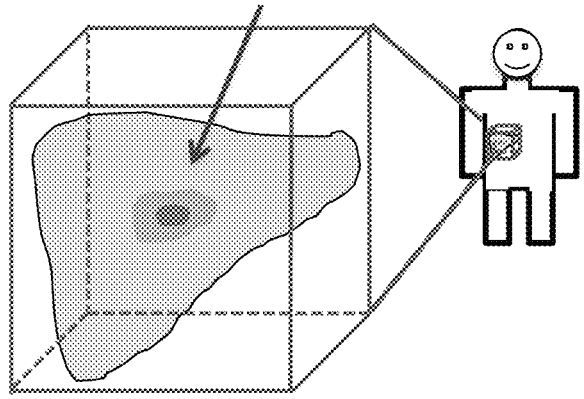

Figure 23

USING TANGIBLE TOOLS TO MANIPULATE 3D VIRTUAL OBJECTS

CROSS REFERENCES TO RELATED APPLICATIONS

This application is a continuation of U.S. patent application Ser. No. 17/181,757 filed on Feb. 22, 2021, which is a continuation in part of U.S. patent application Ser. No. 17/175,815 filed on Feb. 15, 2021, which is a continuation of U.S. patent application Ser. No. 16/843,988 filed on Apr. 9, 2020, which is a continuation of U.S. patent application Ser. No. 16/752,662 filed on Jan. 26, 2020 (issued as U.S. Pat. No. 10,655,731 on May 19, 2020), which is a continuation of U.S. patent application Ser. No. 15/904,092 filed on Feb. 23, 2018 (issued as U.S. Pat. No. 10,586,400 on Mar. 10, 2020).

TECHNICAL FIELD

Aspects of this disclosure are generally related to viewing of volumetric medical images.

BACKGROUND

Traditionally, computed tomography (CT) and magnetic resonance imaging (MRI) scans are viewed by radiologists in a slice-by-slice approach. Recent advances in diagnostic radiology have provided true 3D viewing of medical images through the use of virtual reality, mixed reality or augmented reality headsets and have enabled a volume-by-volume approach and interactive volume subtending 3D cursor usage (See U.S. Pat. No. 8,384,771 for METHOD AND APPARATUS FOR THREE DIMENSIONAL VIEWING OF IMAGES which is incorporated by reference; U.S. Pat. No. 9,980,691 for METHOD AND APPARATUS FOR THREE DIMENSIONAL VIEWING OF IMAGES which is incorporated by reference; and Douglas, D. B., Wilke, C. A., Gibson, J. D., Boone, J. M., & Wintermark, M. (2017). Augmented Reality: Advances in Diagnostic Imaging. Multimodal Technologies and Interaction, 1(4), 29). The interactive, volume-subtending 3D cursor provides more potential at closer examination of sub-volumes within the imaging dataset. Other recent advances include U.S. patent application Ser. No. 16/195,251 for INTERACTIVE VOXEL MANIPULATION IN VOLUMETRIC MEDICAL IMAGING FOR VIRTUAL MOTION, DEFORMABLE TISSUE, AND VIRTUAL RADIOLOGICAL DISSECTION, incorporated by reference, which provides the ability to perform a variety of tissue manipulations to improve visualization and understanding of complex structures. Still further, a set of geo-registered medical imaging tools has been developed (See U.S. patent application Ser. No. 16/524,275 for USING GEO-REGISTERED TOOLS TO MANIPULATE THREE-DIMENSIONAL MEDICAL IMAGES) to manipulate volumes and enhance viewing. However, there are still inherent limitations in the radiologist's ability to interact with volumetric medical images.

SUMMARY

All examples, aspects and features mentioned in this document can be combined in any technically possible way.

In accordance with some aspects a method comprises: for a selected three-dimensional medical image volume loaded in an image processing system, selecting a set of virtual tools from a group of available virtual tools responsive to user input; geo-registering each virtual tool of the selected set with the three-dimensional image volume; and manipulating the three-dimensional image volume in response to manipulation of ones of the set of virtual tools. Some implementations comprise selecting the set of virtual tools from a group of available virtual tools comprising: a virtual focal point pen; a virtual 3D cursor; a virtual transport viewer; a virtual pedestal; a virtual knife; a virtual catheter; a virtual road sign; a virtual ablation tool; a virtual table; a virtual contrast tool; and virtual icons. Some implementations comprise manipulating the three-dimensional image volume responsive to a virtual focal point pen by highlighting a portion of the three-dimensional image volume and adding written notes. Some implementations comprise altering three-dimensional image volume voxels adjacent to a tip of the virtual focal point pen. Some implementations comprise manipulating the three-dimensional image volume responsive to a virtual knife by separating tissue from the three-dimensional image volume. Some implementations comprise manipulating the three-dimensional image volume responsive to the virtual transport viewer by moving the virtual transport viewer within a hollow structure of the three-dimensional image volume and presenting an image from a perspective of the virtual transport viewer. Some implementations comprise using the virtual transport viewer to perform a virtual colonoscopy. Some implementations comprise manipulating the three-dimensional image volume responsive to the virtual contrast material by inserting visible, mobile voxels into the three-dimensional image volume. Some implementations comprise assigning different density values to different ones of the mobile voxels. Some implementations comprise manipulating the three-dimensional image volume in response to manipulation of ones of the set of virtual tools by removing voxels of an outer shell of an organ, which can be performed in a repeated shell-by-shell fashion. Some implementations comprise manipulating the three-dimensional image volume in response to manipulation of ones of the set of virtual tools by spreading apart closely spaced tissue of interest by adjusting coordinates of voxels of the tissue of interest. Some implementations comprise comprising manipulating the three-dimensional image volume responsive to the virtual table by placing tissue of interest in a virtual storage bin of the virtual table. Some implementations comprise manipulating the three-dimensional image volume responsive to the virtual catheter by restricting movement of the virtual catheter to a column of blood voxels within a selected blood vessel. Some implementations comprise automatically displaying information associated with a selected sub-volume of the three-dimensional image volume. Some implementations comprise displaying patient's meta data and current condition for which obtaining the medical image volume was prompted, patient's medical history, laboratory results, and pathology results. Some implementations comprise displaying the information with a virtual windshield. Some implementations comprise displaying distances to key metrics with a virtual road sign. Some implementations comprise displaying a visual aid icon indicating viewing perspective. Some implementations comprise displaying a visual aid icon indicating a finding detected by an artificial intelligence algorithm. Some implementations comprise displaying a visual aid icon indicating location of a sub-volume being displayed relative to the three-dimensional medical image volume or patient's body. Some implementations comprise selecting a sub-volume with a volume-subtending three-dimensional cursor. Some implementations comprise selecting the sub-volume from a plurality of sub-volumes of a predetermined list of sub-volumes. Some implementations comprise sequentially displaying each of the sub-volumes of the list. Some implementations comprise selecting the sub-volume from a plurality of sub-volumes defined by sequential search pattern coordinates. Some implementations comprise selecting the sub-volume from a plurality of sub-volumes defined by random search pattern coordinates. In some implementations manipulating the three-dimensional image volume comprises at least one of: changing voxel size; changing voxel shape; changing voxel position; changing voxel orientation; changing voxel internal parameter; creating a voxel; and eliminating a voxel. In some implementations manipulating the three-dimensional image volume comprises dividing a sub-volume volume of interest into multiple parts based on common characteristics. In some implementations manipulating the three-dimensional image volume comprises generating an exploded view by creating multiple enlarged cubes each touching a center point. Some implementations comprise employing a virtual eye tracker symbol to assist in human eye viewing. Some implementations comprise making the virtual eye tracker symbol appear and disappear at spatially separate lactations so that the human eye can perform saccades and jump from one location to another. Some implementations comprise making the virtual eye tracker symbol move smoothly along a path, so that the human eye can perform smooth tracking.

In accordance with some aspects an apparatus comprises: an image processing system comprising an interface that presents, for a selected three-dimensional medical image volume loaded in the image processing system, a set of virtual tools for selection from a group of available virtual tools responsive to user input, geo-registers each virtual tool of the selected set with the three-dimensional image volume, and an image processor that manipulates the three-dimensional image volume in response to manipulation of ones of the set of virtual tools. In some implementations the set of virtual tools is selected from a group of available virtual tools comprising: a virtual focal point pen; a virtual 3D cursor; a virtual transport viewer; a virtual pedestal; a virtual knife; a virtual catheter; a virtual road sign; a virtual ablation tool; a virtual table; a virtual contrast tool; and virtual icons. In some implementations the set of virtual tools comprises a virtual focal point pen and the image processor manipulates the three-dimensional image volume responsive to the virtual focal point pen by highlighting a portion of the three-dimensional image volume and adding written notes. In some implementations the image processor alters three-dimensional image volume voxels adjacent to a tip of the virtual focal point pen. In some implementations the set of virtual tools comprises a virtual knife and the image processor manipulates the three-dimensional image volume responsive to the virtual knife by separating or manipulating (e.g., changing the location of) voxels (e.g., tissue-type voxels) from the three-dimensional image volume. In some implementations the set of virtual tools comprises a virtual transport viewer and wherein the image processor manipulates the three-dimensional image volume responsive to the virtual transport viewer by moving the virtual transport viewer within a hollow structure of the three-dimensional image volume and presenting an image from a perspective of the virtual transport viewer. In some implementations the virtual transport viewer is used to perform a virtual colonoscopy via the interface. In some implementations the set of virtual tools comprises a virtual contrast material and the wherein the image processor manipulates the three-dimensional image volume responsive to the virtual contrast material by inserting visible, mobile voxels into the three-dimensional image volume. In some implementations the image processor assigns different density values to different ones of the mobile voxels. In some implementations the image processor manipulates the three-dimensional image volume in response to manipulation of ones of the set of virtual tools by removing voxels of an outer shell of an organ. In some implementations the image processor manipulates the three-dimensional image volume in response to manipulation of ones of the set of virtual tools by spreading apart closely spaced tissue of interest by adjusting coordinates of voxels of the tissue of interest. In some implementations the set of virtual tools comprises a virtual table and the image processor manipulating the three-dimensional image volume responsive to the virtual table by placing tissue of interest in a virtual storage bin of the virtual table. In some implementations the set of virtual tools comprises a virtual catheter and the image processor manipulates the three-dimensional image volume responsive to the virtual catheter by restricting movement of the virtual catheter to a column of blood voxels within a selected blood vessel. In some implementations the interface automatically displays information associated with a selected sub-volume of the three-dimensional image volume. In some implementations the interface displays patient's meta data and current condition for which obtaining the medical image volume was prompted, patient's medical history, laboratory results, and pathology results. Some implementations comprise the interface displaying the information with a virtual windshield. Some implementations comprise the interface displaying distances to key metrics with a virtual road sign. Some implementations comprise the interface displaying a visual aid icon indicating viewing perspective. Some implementations comprise the interface displaying a visual aid icon indicating a finding detected by an artificial intelligence algorithm. Some implementations comprise the interface displaying a visual aid icon indicating location of a sub-volume being displayed relative to the three-dimensional medical image volume or patient's body. Some implementations comprise the interface receiving selection of a sub-volume with a volume-subtending three-dimensional cursor. In some implementations the selected sub-volume is one of a plurality of sub-volumes of a predetermined list of sub-volumes. Some implementations comprise the interface sequentially displaying each of the sub-volumes of the list. In some implementations the selected sub-volume is one of a plurality of sub-volumes defined by sequential search pattern coordinates. In some implementations the selected sub-volume is one of a plurality of sub-volumes defined by random search pattern coordinates. In some implementations the image processor manipulates the three-dimensional image volume comprises at least one of: changing voxel size; changing voxel shape; changing voxel position; changing voxel orientation; changing voxel internal parameter; creating a voxel; and eliminating a voxel. In some implementations the image processor manipulates the three-dimensional image volume by dividing a sub-volume volume of interest into multiple parts based on common characteristics. In some implementations the image processor manipulates the three-dimensional image volume by generating an exploded view by creating multiple enlarged cubes each touching a center point. In some implementations the interface comprises a virtual eye tracker symbol. In some implementations the virtual eye tracker symbol appears and disappears at spatially separate lactations so that the human eye can perform saccades and jump from one location to another. In some implementations the virtual eye tracker symbol moves smoothly along a path.

In some implementations, a method and apparatus for preparing software to implement the virtual tool kit for enhanced medical image analysis is employed, which comprises the following steps: loading volumetric medical imaging dataset in accordance with a checklist, converting the medical images to a 3D volume and importing a virtual tool kit; performing registration and calibration of each virtual tool with/within the geo-registered volumetric medical image; performing filtering, segmentation and voxel manipulations (e.g. as described in U.S. patent application Ser. No. 15/904,092 for PROCESSING 3D MEDICAL IMAGES TO ENHANCE VISUALIZATION and U.S. patent application Ser. No. 16/195,251 which are incorporated by reference and advanced viewing options taught in the present disclosure); for every time step, providing displays in accordance with movement and operation of the virtual tool kit listed in steps above; a decision point is reached wherein either the checklist is complete in which case one can go to the next step or the examination is not complete and one returns to the previous step; and, finally if the review of the entire set of medical is complete, then the examination is terminated and the report is prepared and filed.

An apparatus comprising: an IO device; an image processor in communication with the IO device, the image processors comprising a program stored on computer-readable non-transitory media, the program comprising: instruction to perform of segmentation of the voxels into distinct tissue types; instruction to perform voxel manipulations; instructions to creation and insertion of at least one additional voxel into the medical imaging dataset; instructions to eliminate voxel into the medical imaging datasets; instructions to perform voxel annotations to the above user-altered radiologic image; instructions to recording steps for review.

In some implementations, virtual tool maneuvers can also be accomplished via the controller/joystick input. In some implementations, the controller/joystick input can direct the 3D cursor to change size, shape, or orientation (roll, pitch and yaw). In some implementations, controller/joystick input can direct the left and the right eye viewing perspectives to be zoomed inward towards the 3D cursor or out away from the cursor. In some implementations, controller/joystick input can direct convergence to a focal point. In some implementations, controller/joystick input can direct raising or lowering of the 3D cursor within the head display unit, or moving the 3D cursor from side to side. In some implementations, controller/joystick input can change the color of the 3D cursor. In some implementations, controller/joystick input can invoke filtering, segmentation, sequencing, statistical analysis and reporting, which were discussed in U.S. patent application Ser. No. 15/904,092, which is incorporated by reference. In some implementations, controller/joystick input can direct movement of a virtual focal point pen through the volume of interest. In some implementations, controller/joystick/keyboard input can direct annotations of one or more 3D cursors within the volume of interest. In some implementations, controller/joystick input can direct icon options as related to the volumetric medical imaging to keep the radiologist organized in his/her checklist approach to a complex exam. In some implementations, presenting 3D medical images comprises a method of improved user controller interface for medical personnel reviewing 3D medical images comprised of joystick and functional buttons. Functionality would include, but is not limited to, the following when interfacing with the 3D cursor: change the orientation of the 3D cursor—roll, pitch and yaw; zoom the medical person viewpoint in toward the 3D cursor and out away from the cursor; invoke convergence; raise and lower the 3D cursor as to where it is displayed on the headset; change the size, shape, and color of the 3D cursor; invoke filtering, segmentation, sequencing, statistical, and reporting operations; invoke virtual focal point pen and movement control thereof; annotate one or more 3D cursors within the volume of interest; invoke icon options; and, invoke advanced viewing options of interest (e.g., explosion, ablation, slice-type viewing). A representative sample of virtual tools includes, but is not limited to the following: virtual focal point pen; virtual 3D cursor; virtual transport viewer; virtual pedestal; virtual knife; virtual catheter; virtual road signs; virtual ablation; virtual table; virtual contrast; and, virtual icons. Many other virtual tools, are possible, but are not illustrated, which include, but are not limited to, the following: drill; cup; string; mirror; lens; metallic devices; non-metallic devices; and other tools, commonly used by medical personnel, construction workers or engineers.

In some implementations, the medical person conducting the review of volumetric medical images could invoke a process whereby a virtual radiology assistant type icon is displayed. The purpose of the virtual radiology assistant type icon is to portray all relevant/important information relating to inter alia: where the medical person conducting the examination is on the medical institution's checklist and what's next; patient's meta data and current condition triggering obtaining medical image(s); patient's medical history; laboratory results; results, if any, from application of artificial intelligence (AI) routines and indicators of condition. In this implementation, the medical person conducting the review could command display of the virtual windshield at any time. In this implementation, the medical person conducting the review could also modify items to be shown on the windshield.

In some implementations, virtual tools can direct voxel alterations. Examples of voxel manipulations include changing the size, shape, position, orientation or internal parameter of a voxel. Furthermore, voxels can be created or eliminated at the direction of the virtual tool.

In some embodiments, a virtual focal point pen is utilized to enhance visualization of a structure of interest within the medical imaging volume. In some implementations, the focal point pen can be used to point to areas within the structure, which may contain anomalies. In some implementations, the focal point pen can use symbols (e.g., arrows) to point to the areas of interest. In some implementations, notes can be written in the volumetric data. In some implementations, voxels in proximity of the point of the focal point pen can be highlighted in conjunction with modifying the transparency of tissues at a specified distance away from the tip of the focal point pen. In some implementations, the focal point pen can be used in conjunction with the 3D cursor.

In some embodiments, a virtual eye tracker symbol is employed with the 3D medical imaging dataset to facilitate the human in viewing structures. In some embodiments, the virtual eye tracker symbol appears and disappears at spatially separate lactations so that the human eye can perform saccades and jump from one location to another. In another embodiments, the virtual eye tracker symbol is continuously visible and has a smooth movement along a path, so that the human eye can perform smooth tracking. The virtual eye tracker symbol can be controlled by, but not limited to, the following: virtual tool (e.g. virtual focal point pen); geo-registered tool; or, a pre-programmed sequence. A tangible geo-registered tool can be held in a user's hand. The user can maneuver the tangible geo-registered tool to manipulate a three-dimensional image volume's visual appearance or structure.

In some implementations, a virtual knife can be co-registered with the volumetric medical images and used to cut virtual tissue in a medical imaging volume. In a further implementation, the virtual knife would have a moveable geo-registration point (e.g., tip of the virtual knife), additional points to indicate the cutting surface of the virtual knife and the control unit would provide changes in the X, Y, Z coordinate system and also roll, pitch and yaw of the knife. The virtual knife could be used, but not limited to, as follows: the medical person viewing the medical images could: pick up the virtual knife and move it to the 3D digital structure of current interest, then pass the virtual knife through the 3D geo-registered structure, and tissue may be deleted (or set aside) which is external to the surface created by virtual knife when it passed through the 3D geo-registered structure (the side of the virtual knife pre-selected by the medical person viewing the medical images). In further implementation, the virtual knife would have an exact registration point (e.g., tip of geo-registered knife), additional geo-registration points to indicate the cutting surface of the knife. In some implementations, tactile or auditory feedback can be provided to the user.

In some implementations, presenting 3D medical images comprises a method to facilitate viewing medical images consisting of using a visual transport tool to achieve a ride through a blood vessel. In a further implementation, the virtual catheter could be used in conjunction with a visual transport tool to optimize viewing of the vascular structure within the patient. Example procedures include but, are not limited to the following: the ride in a tunnel could be used during an assessment of the vascular structure and potential need for insertion of one or more stents. In this case, the ride in a blood vessel entry could be through the groin into the common femoral artery, external iliac artery, common iliac artery, abdominal aorta, thoracic aorta, aortic arch, and finally the coronary artery of interest. Then, the medical person viewing the medical images visualize what it looks like to travel within a blood vessel as viewed from a 3D headset. Blood within the blood vessel could be digitally subtracted and a virtual light could shine on the blood vessel walls. Constrictors within the vascular structure would show up as a narrowing of the tunnel and X, Y, Z coordinates of the constrictor be recorded. At any time the medical person viewing the medical images could view the vascular structure as a whole with current location of the ride in the blood vessel shown. In some implementations, the diameter of the blood vessel could be expanded and voxels manipulated such that optimal viewing of the internal structure is achieved. In some implementations, presenting 3D medical images comprises a method to facilitate viewing medical images consisting of a 3D geo-registered ride in the blood vessel. In further implementation, this 3D geo-registered ride in the tunnel would be used in conjunction geo-registration of patients as described in U.S. patent application Ser. No. 15/949,202 for SMART OPERATING ROOM EQUIPPED WITH SMART SURGICAL DEVICES and U.S. patent application Ser. No. 16/509,592 for IMPLANTABLE MARKERS TO AID SURGICAL OPERATIONS. The interventionist could switch back and forth between the geo-registered 3D system using the 3D head mounted display and standard displays currently available in interventional operations. This permits viewing in near real time the constrictors identified during pre-operative planning. Further, alerts could be given in near real time as critical junctions were being approached.

In some implementations, presenting volumetric medical images comprises a method to facilitate viewing medical images consisting of a virtual catheter. In further implementation, the virtual catheter could be used in conjunction with a 3D digital image of the vascular structure within the patient. In further implementation, the catheter could continuously compute the total distance travelled which could be displayed, and also time tagged and recorded for later review. The virtual catheter could be used during pre-operative planning of an interventional procedure such as, but not limited to, treatment of a cerebral aneurysm. Implementation of the virtual catheter in treatment of an aneurysm could be as follows: insert the virtual catheter into the 3D digital vascular structure at a pre-determined point such as the groin of the patient into the common femoral artery, then the external iliac artery, then the common iliac artery, then the abdominal aorta, then the thoracic aorta, then the brachiocephalic artery, then the common carotid artery, then the internal carotid artery then the middle cerebral artery, and finally into the aneurysm. Augmented reality distance markers could be added to the 3D virtual catheter for each intersection the interventionalist would need to take care and be prepared to change from one blood vessel to another; screen captures of all key vascular junctures could be annotated angular changes from current path in coordinate system X-Y, X-Z and Y-Z planes.

In some implementations, presenting 3D medical images comprises a method to facilitate viewing medical images consisting of an explosion within the 3D digital imagery. In further implementation, the medical person viewing the medical images (e.g., using segmentation techniques outlined in U.S. patent application Ser. No. 15/904,092) could divide the 3D digital volume of interest into multiple parts based on their common characteristics (e.g., similar Hounsfeld units). Then the medical person viewing the medical images could select a point within the 3D digital volume (ideally near the center of the 3D digital volume and between segmented sub-volumes) which would act at the origin point for the explosion. Then, there are multiple ways the sub-volumes of the 3D digital can be separated as if an explosion occurred. One of the ways, but not limited to, is as follows: create eight large cubes each touching the center point and each parallel to the X, Y, Z axes (e.g., the first cube would be positive in X, positive in Y and positive in Z; the second cube could be positive in X, negative in Y and positive in Z; and so on). Then the medical person viewing the medical images establishes a distance factor for sub-volumes close to the center point, a larger distance factor for those further away. Then these factors are applied to all voxels within each specific sub-volume of the 3D digital image based on which cube the center voxel of the sub-volume was in. (Note that for the first cube mentioned above, for all sub-volumes whose center voxel fell in this cube the X, Y, Z coordinates of voxels within that sub-volume would increase by the specified factor in the positive X, positive Y and positive Z direction. For sub-volumes in the second cube the increases would be in positive X, negative Y and positive Z directions). The medical person viewing the medical images modify the factors changing the spread between the sub-volumes during the course of the examination.

In some implementations, the virtual transport process viewer could be used to precede a colonoscopy. Under the virtual transport viewer process, the patient would: first receive a CT scan of the colon; a 3D volume of the colon would be created from the CT 2D slices (U.S. Pat. No. 8,384,771); segmentation (U.S. patent application Ser. No. 15/904,092) would identify and subtraction would extract the contents of the colon (e.g., air, excrement) and in so doing the colon would maintain its original shape and any polyps would be visible; then the virtual platform could be inserted and enable examination back and forth and side to side within the colon. For ease of 3D viewing, the diameter of the colon could be increased thru voxel manipulation (U.S. patent application Ser. No. 16/195,251) to an optimal diameter from the center point of the enlarged colon. If no polyps were found, the patient could go home confident of continued good health and he/she would have avoided the unpleasantness and discomfort of a colonoscopy and the cost of the colonoscopy avoided. Otherwise, treatment would be known to be required. Personnel who would have avoided the colonoscopy would likely not shy away from the virtual transport viewer process and the fraction of cases wherein detection occurred at an early stage would increase. Thereby, the general health of the populace would be improved.

In some implementations, the medical person conducting the review of volumetric medical images of the colon could invoke a process whereby a virtual colonoscopy is performed. In this implementation, a CT scan of the colon with/without contrast is performed. Then a 3D virtual image is constructed from the CT 2D slices (U.S. Pat. No. 8,384,771). Segmentation (U.S. patent application Ser. No. 15/904,092) is performed and tissue subtracted external to the colon. Also, the non-tissue contents within the colon are subtracted. Then the colon is 'stretched' so that folds which can obscure polyps are elongated and, thereby, obscuration of polyps by folded colon tissue is eliminated. This stretching process involves voxel manipulation as described in U.S. patent application Ser. No. 16/195,251. This elongated, straight virtual colon is split in 2 along the length axis so that the internal structure can be viewed via the head display unit as illustrated in this figure.

In some implementations, presenting 3D medical images comprises a method to facilitate viewing medical images consisting of insertion of virtual contrast material within the vascular system. In further implementation, the virtual contrast could be used in conjunction with a 3D digital image of the vascular structure within the patient. Example procedures include, but are not limited to, the following: search for blockage as in a pulmonary embolism. In this example, blood vessels would be selected to receive the virtual contrast material in a time step fashion. Insertion of the virtual contrast could be in a manner and velocity as if it were actually being inserted into the blood vessel. The duration of the time step would be under the control of medical person viewing the medical images; 'freeze frame' would be available together with replay of the contrast flow. Nearby and possibly overlapping blood vessels other than the one receiving the virtual contrast, could be extracted from the 3D imagery displayed to medical person viewing the medical images.

In some implementations, presenting 3D medical images comprises a method to facilitate viewing medical images consisting of an ablation technique. In further implementation, the ablation technique could be used in conjunction with 3D digital structure, transported by the 3D cursor as described above. The method underlying the ablation technique consists of, but not limited to, the following procedures: first determine the outer 'shell' of organ of interest to the medical person viewing the medical images (e.g., using segmentation techniques outlined in U.S. patent application Ser. No. 15/904,092); sequentially eliminate one voxel deep from all of the voxels on the outer surface—repeat this step multiple times on the remaining outer layer of tissue at the direction of the medical person viewing the medical images; alternatively, select one layer in the X, Y, Z coordinate system (e.g., select the X-Y layer with the highest Z coordinate and eliminate that layer—repeat this step multiple times on the remaining 3D digital volume at the direction of the medical person viewing the medical images. This process can be repeated multiple times and each time the outer shell is removed, leaving a slightly smaller volume. Then, the process is repeated again and the new, smaller outer shell is removed once again leaving an even smaller volume. And so on.

In some implementations, the virtual tool can be utilized to alter the location of tissue of interest that is closely spaced such that the separation distance of these tissues can be increased through voxel manipulation (e.g., insertion of additional voxels of varying transparency) and concurrently adjusting the coordinates of the tissues of interest.

In some embodiments, a sub-volume-by-sub-volume viewing approach is enabled. Sub-volumes can be made from varying number or combination of voxels.

In some implementations, presenting 3D medical images comprises a method to sequence the movements of the 3D cursor through the volume of interest. The sequence could, for example but not limited to, start the 3D cursor located at the 0_X, 0_Y, 0_Z coordinate, increment X to move the 3D cursor in the X direction and continue to increment to the maximum value of X, then increment Y and decrement X back to the OX coordinate. This would continue through the X-Y plane until it was completed, then Z would be incremented, and the process continued until completion. The increments would continue until the entire volume of interest had been reviewed. Changing from one increment to another would be controlled by the medical personnel reviewing the medical images. Further, during the review of the contents of the 3D cursor, if suspicious tissue were detected, the medical personnel could annotate the 3D cursor for further review. Further, at any time the medical personnel could choose to display the location of where the 3D cursor is within the volume of interest and the volume of interest that had already been examined. In the event suspicious tissue appeared in more than one 3D cursor, the totality of these 3D cursors could be displayed simultaneously. In some implementations, the medical person reviewing the 3D virtual medical image may invoke a type of search pattern. In some implementations, a sequential search pattern may be selected. An example of sequential search is, but not limited to, a virtual windshield wiper search. This type of search pattern helps ensure a thorough search has been conducted. In some implementations, random pattern based on examining items of possible interest. Image processing aids such as changing organ transparency and using false color can help identify items of potential interest (U.S. Pat. No. 8,384,771). This type of search pattern can expedite the review process. Both types of search patterns employ a 3D cursor (U.S. Pat. No. 9,980,691 for METHOD AND APPARATUS FOR THREE DIMENSIONAL VIEWING OF IMAGES and U.S. patent application Ser. No. 15/878,463 for INTERACTIVE 3D CURSOR FOR USE IN MEDICAL IMAGING). Note: when reviewing medical images in the original 2D format, the eyes jump from one spot to another following the reviewing individual's saccadian path and substantial portions of a slice may not be observed and, consequently, small masses may be missed. In the use of the 3D cursor, these small masses subtend a larger fraction of presented image and the probability of detection increases proportionally.

In some implementations, the medical person conducting the review of volumetric medical images could invoke a process whereby a volumetric medical image is examined using a step-by-step process of selection of sub-volumes (of the total volume) that are encased within the 3D cursor (U.S. Pat. No. 9,980,691 and U.S. patent application Ser. No. 15/878,463). Each 3D cursor's contents would be independently reviewed. Further, after the step-by-step process has been completed, the question could arise as to whether the entire volume has been examined. In this implementation, the volume contained in each of the 3D cursors which had been examined could be totaled and subtracted from the total original volume. This could result is some portions of the original volume being missed. In this implementation, these missed portions would be highlighted to the medical person performing the review and he/she could be alerted to continue the review and examine missed portions. Under this implementation, the detection rate of small mass would increase when compared to the 2D slice examination process. Under this implementation, a more thorough examination would have been performed. In some implementations, presenting 3D medical images comprises a method to sequence the movements of the 3D cursor through the volume of interest. The sequence could, for example but not limited to, start the 3D cursor located at the 0_X, 0_Y, 0_Z coordinate, increment X to move the 3D cursor in the X direction and continue to increment to the maximum value of X, then increment Y and decrement X back to the OX coordinate. This would continue through the X-Y plane until it was completed, then Z would be incremented, and the process continued until completion. The increments would continue until the entire volume of interest had been reviewed. Changing from one increment to another would be controlled by the medical personnel reviewing the medical images. Further, during the review of the contents of the 3D cursor, if suspicious tissue were detected, the medical personnel could annotate the 3D cursor for further review. Further, at any time the medical personnel could choose to display the location of where the 3D cursor is within the volume of interest and the volume of interest that had already been examined. In the event suspicious tissue appeared in more than one 3D cursor, the totality of these 3D cursors could be displayed simultaneously.

In some implementations, virtual icons can be used in conjunction with viewing of the medical imaging volume to facilitate orientation. As an example, during close inspection of a small region of an organ (e.g. liver), one can become slightly disoriented as to where precisely within the organ the 3D cursor is located. Thus, the icon can assist with orientation at all times during the viewing of the examination. In another embodiment, an arrow annotation marker can show the path from the initial viewing perspective to the current viewing perspective. In an alternative embodiment, an auto-recenter technique can be used to quickly reorient the user.

In some implementations, a virtual table could be added to the tool kit which would have virtual storage bins on the table. Sub-volume(s) of the virtual medical image which is currently being examined and which contain tissue of concern/interest could be placed in the virtual storage bin(s). The bins for the sub-volumes could correspond to checklist items of the medical institution. In some implementations, an emergency bin could be added which could be accessed by both reviewing medical person and treatment personnel, thereby facilitating and expediting collaboration between these persons. In some implementations, the report preparation could be expedited by automatically sequencing through the bins and, extracting items, and adding these items to the report. The added items (e.g., an annotated figure containing the tissue in question) would add to both the quality and completeness of the report. Anytime a radiologist finds something anomalous, he/she puts it on the report virtual table. The item placed on the report virtual table may include the 2D slice or the 3D volume containing the anomalous finding. The radiologist has options to determine the size of the virtual table and virtual bins. One radiologist can pass an item onto another radiologist's table or bin for collaboration.

In some implementations, a radiology report may include images processed via virtual tools.

BRIEF DESCRIPTION OF THE FIGURES

FIG. 9A illustrates a virtual ride thru virtual blood vessel using a visual transport tool at a first position.

FIG. 9B illustrates a virtual ride thru virtual blood vessel using a visual transport tool at a second position.

FIG. 9C illustrates a virtual ride thru virtual blood vessel using a visual transport tool at a third position.

FIG. 10A illustrates the virtual catheter could be used in conjunction with a volumetric medical image of the vascular structure within the patient with the assistance of virtual icons wherein the virtual catheter is at a first position.

FIG. 10B illustrates the virtual catheter could be used in conjunction with a volumetric medical image of the vascular structure within the patient with the assistance of virtual icons wherein the virtual catheter is at a second position.

FIG. 10C illustrates the virtual catheter in relation to a vascular structure.

FIG. 12A illustrates use of virtual transport viewer at a first position to perform a more accurate virtual colonography review.

FIG. 12B illustrates use of virtual transport viewer at a first position to perform a more accurate virtual colonography review.

FIG. 14A illustrates insertion of virtual contrast and its flow through the vascular system at a first time point.

FIG. 14B illustrates insertion of virtual contrast and its flow through the vascular system at a second time point.

FIG. 14C illustrates insertion of virtual contrast and its flow through the vascular system at a third time point.

FIG. 14D illustrates insertion of virtual contrast and its flow through the vascular system at a first time point wherein there is a blood clot within a branch.

FIG. 14E illustrates insertion of virtual contrast and its flow through the vascular system at a second time point wherein there is a blood clot within a branch.

FIG. 14F illustrates insertion of virtual contrast and its flow through the vascular system at a third time point wherein there is a blood clot within a branch.

FIG. 15 illustrates an ablation technique could be used, inter alia, in conjunction with 3D digital structure within a 3D cursor. This permits careful examination of the interior structure and elements of an organ.

FIG. 23 illustrates a sample radiology report including an image processed with virtual tools.

DETAILED DESCRIPTION

Some aspects, features and implementations described herein may include machines such as computers, electronic components, radiological components, optical components, and processes such as computer-implemented steps. It will be apparent to those of ordinary skill in the art that the computer-implemented steps may be stored as computer-executable instructions on a non-transitory computer-readable medium. Furthermore, it will be understood by those of ordinary skill in the art that the computer-executable instructions may be executed on a variety of tangible processor devices. For ease of exposition, not every step, device or component that may be part of a computer or data storage system is described herein. Those of ordinary skill in the art will recognize such steps, devices and components in view of the teachings of the present disclosure and the knowledge generally available to those of ordinary skill in the art. The corresponding machines and processes are therefore enabled and within the scope of the disclosure.

Figure 1:
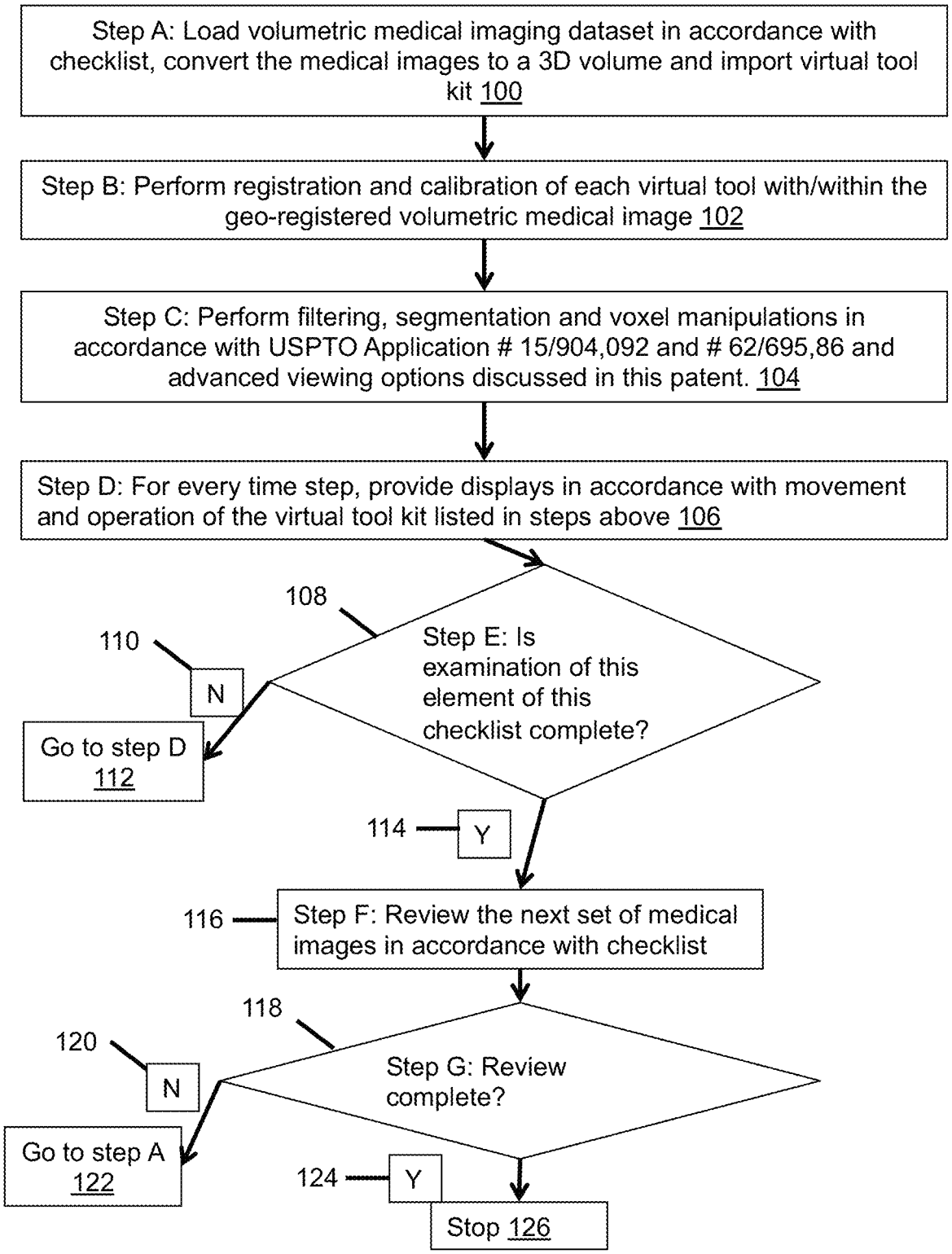
FIG. 1 illustrates a flow diagram for the use of virtual tools to optimize display of medical imaging examinations.

FIG. 1 illustrates a flow diagram for the use of geo-registered tools to optimize display of medical imaging examinations. In Step A 100, load volumetric medical imaging dataset in accordance with checklist, convert the medical images to a 3D volume and import virtual tool kit. In Step B 102, perform registration and calibration of each virtual tool with/within the geo-registered volumetric medical image. In step C 104, perform filtering, segmentation and voxel manipulations in accordance with U.S. application Ser. No. 15/904,092 and U.S. patent application Ser. No. 16/195,251, which are incorporated by reference, and advanced viewing options discussed in this disclosure. In Step D 106, for every time step, provide displays in accordance with movement and operation of the virtual tool kit listed in steps above. In step E 108, the user must answer the question of "is the examination of this element of the checklist complete?" If the answer is no 110, then the user should proceed to step D 106. If the answer is yes 114, then the radiologist should proceed to step F 116 and review the next set of medical images in accordance with the checklist. Then the radiologist should proceed to step G 118 and answer the question of "is the review complete?" If the answer is no 120, then the radiologist should go 122 to step A 100. If the answer is yes 124, then the radiologist should stop 126.

Figure 2:
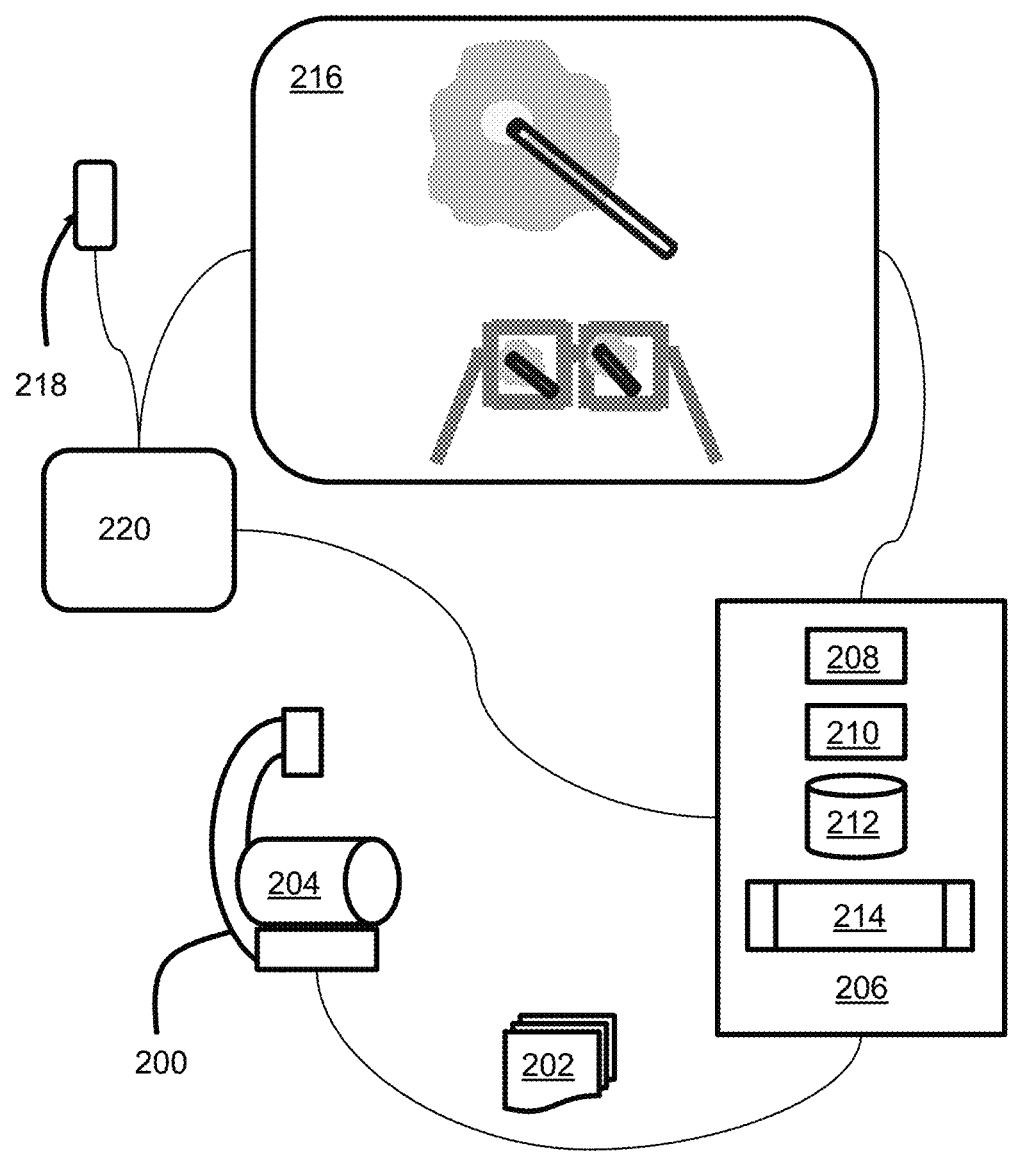
FIG. 2 illustrates an apparatus for implementing the process of FIG. 1.

FIG. 2 illustrates an apparatus for implementing the process illustrated in FIG. 1. A radiologic imaging system 200 (e.g., X-ray, ultrasound, CT (computed Tomography), PET (Positron Emission Tomography), or MRI (Magnetic Resonance Imaging)) is used to generate 2D medical images 202 of an anatomic structure 204 of interest. The 2D medical images 202 are provided to an image processor 206, that includes processors 208 (e.g., CPUs and GPUs), volatile memory 210 (e.g., RAM), and non-volatile storage 212 (e.g. HDDs and SSDs). A program 214 running on the image processor implements one or more of the steps described in FIG. 1. 3D medical images are generated from the 2D medical images and displayed on an IO device 216. The IO device 216 may include a virtual reality headset, mixed reality headset, augmented reality headset, monitor, tablet computer, PDA (personal digital assistant), mobile phone, or any of a wide variety of devices, either alone or in combination. The IO device 216 may include a touchscreen, and may accept input from external devices (represented by 218) such as a keyboard, mouse, and any of a wide variety of equipment for receiving various inputs. However, some or all the inputs could be automated, e.g. by the program 214. Finally, as discussed further in FIG. 3 and the rest of this patent, a series of virtual tools 220 are implemented, which facilitate viewing of medical images by medical personnel.

Figure 3:
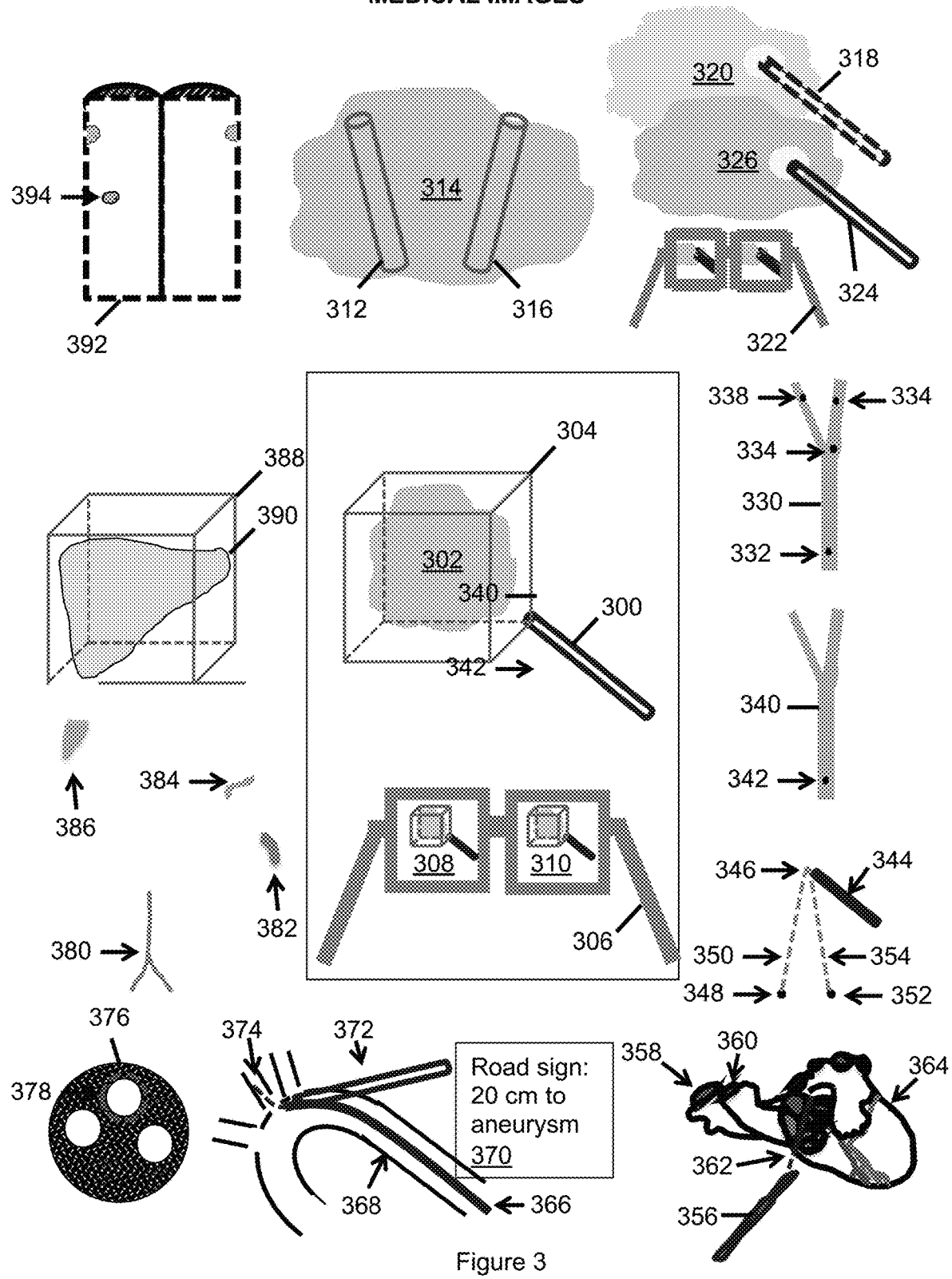
FIG. 3 illustrates virtual toolkit options in viewing volumetric medical images.

FIG. 3 illustrates virtual toolkit options in viewing volumetric medical images. In this figure, representative examples of viewing options available through the use of a virtual tools are illustrated. Options by which the virtual tools can be guided/selected could be presented on the display and the user would click on desired option. In the center of the illustration, the virtual tool 300 (i.e., virtual focal point pen) is geo-registered within the medical imaging volume. The virtual focal point pen is superimposed within the region containing the virtual 3D medical image 302 located inside of the 3D cursor 304. A button (e.g., on the keyboard) plus a movement of a virtual tool can be coupled together to size the 3D cursor 304 (e.g., select the center of the 3D cursor 304 and then move the virtual focal point pen 300 a distance away to correspond to the radius). The user views the virtual tool using a headset 306 (e.g., augmented reality, mixed reality or virtual reality) glasses with a left eye display 308 and right eye display 310. The virtual focal point pen can be registered within the virtual image by touching specific spots (e.g., corners) of the medical imaging volume 302. For display purposes, the medical personnel can select to only show the tip of the focal point pen in the display, enlarge the tip of the focal point pen as desired, and/or show the virtual image of the focal point pen in its entirety as it is oriented within the volume. Movement of the virtual focal point pen 300 would be controlled by medical person viewing the medical images. The virtual focal point pen 300 is useful when smooth pursuit eye movements are necessary. For example, smooth pursuit eye movements are necessary when examining arteries for any blockages, wherein using the virtual focal point pen to trace along arteries looking for blockages. Saccadian eye movement could result in skipping over portions of the artery and a serious blockage go undetected; therefore, the virtual focal point pen 300 could be helpful in aiding this search pattern. Multiple colored/shaped virtual focal point pens 300 could be used to trace the different flows of arteries and veins. In the top image, the position and orientation of the virtual tool changes with respect to the volume of interest. The virtual focal point pen is shown with an initial position and orientation 312 with respect to the volume of interest 314. Then, the user can move the virtual focal point pen to a subsequent position and orientation 316 with respect to the volume of interest 314. Proceeding clockwise, next the virtual focal point pen 318 performs grabbing of the volume of interest 320 at an initial distance from the head display unit 322. Then, the virtual vocal point pen 324 pulls the volume of interest 326 closer to the head display unit 322 for improved visualization. Alternatively, the volume of interest 320 could be moved in other positions or orientations by the focal point pen 318. Next, a virtual dot can be placed on or next to a portion of the virtual image 330 (e.g., carotid artery) being examined in a fixed or dynamic manner. For example, the dot can appear and disappear at multiple spots along the vascular structure to facilitate Saccadian viewing where the eyes jump short distances to view the most important portions of the vascular structure. At time point #1, a first virtual dot 332 appears and no other virtual dots are shown in the field of view at this time. At time point #2, a second virtual dot 334 appears and no other virtual dots are shown in the field of view at this time. At time point #3, a third virtual dot 336 appears and no other virtual dots are shown in the field of view at this time. At time point #4, a fourth virtual dot 338 appears and no other virtual dots are shown in the field of view at this time. Alternatively, the virtual dot 342 can be moving along a portion of the virtual image 340 (e.g., carotid artery) to help the human eye perform smooth tracking and enhanced viewing of the vascular structure. Next, the virtual focal point pen 344 is used to perform convergence to a focal point 346. A left eye view point 348 is shown. A line illustrating the look angle of the left eye 350 is also shown. A right eye view point 352 is shown. A line illustrating the look angle of the right eye 354 is also shown. Note that the look angle 350 from the left eye view point 348 and the look angle 354 from the right eye view point 352 intersect at the convergence point 346. Next, a virtual dissection is performed by using a virtual knife 356 and the aorta 358 and pulmonary artery 360 are cut and moved away from the rest of the heart 364. Note the cutting plane 362 is shown. Next, a virtual catheter 366 is being placed through the aorta 368 within the medical imaging volume. Note that a virtual road sign 370 is shown to guide the medical personnel. The focal point pen 372 is shown. The dotted line blue line 374 is the desired catheter trajectory, which can be at different time setting. The virtual catheter 366 can be pulled through the vascular system. A ride through the blood vessel type viewing is shown 376 with the desired path highlighted in a dotted red circle 378. The last three examples illustrate advanced viewing options enabled by the virtual tools. An explosion-type viewing where the organs are separated is illustrated wherein the various organs are separate. For example, the amount of spacing between the various abdominal organs including the aorta 380, left kidney 382, pancreas 384 and liver 386 is increased. Next, a virtual ablation is performed wherein the outer shell 390 of a virtual tissue are sequentially removed over multiple time points. The anatomic structure in which virtual ablation is performed can be placed in a 3D cursor 388 to help direct the ablation. Finally, a structure such as the colon 392 can be sliced (e.g., using a virtual knife) and opened such that the inner aspects including a polyp 394 inside the hollow viscus can be more carefully examined. Voxel manipulation would be required to achieve this aspect.

Figure 4:
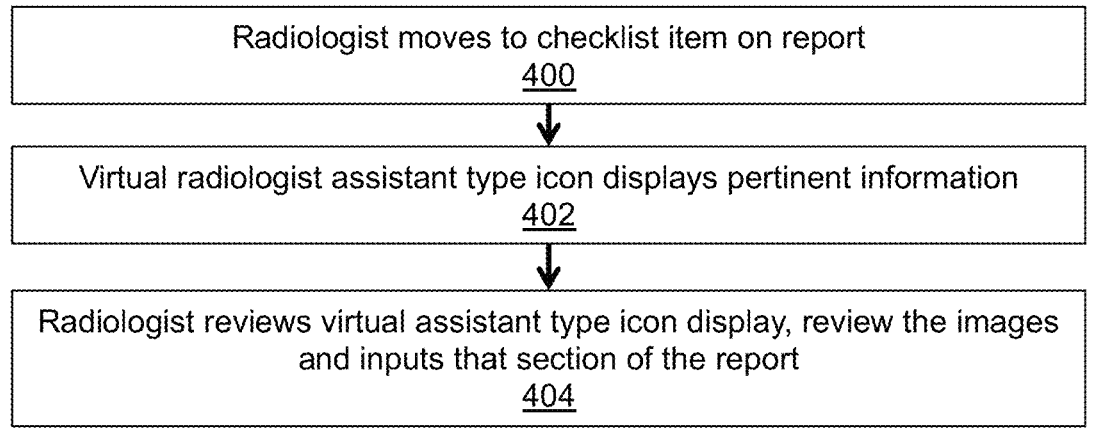
FIG. 4 illustrates a flow diagram and an example heads-up display type icon delivering pertinent information to the radiologist during the interpretation of the imaging examination. The heads-up display we refer to as a virtual windshield (analogous to a 'heads-up' display in an aircraft) which could be called at any time during the examination process and would display on a single virtual windshield items relevant to the patient's entire case and/or the particular item being examined on the medical institution's checklist. Alternatively, it can be referred to as a virtual radiology assistant type icon.

FIG. 4 illustrates a flow diagram and an example heads-up display type icon delivering pertinent information to the radiologist during the interpretation of the imaging examination. First a flow diagram is illustrated to show how the virtual windshield 406 can be used to assist with interpretation of the radiology images. The first step 400 is for the radiologist (or other medical personnel) to move to a checklist item on the report. The second step 402 is for the virtual assistant type icon (also known as the virtual windshield 406) to display the pertinent information. The third step 404 is for the radiologist to review the virtual assistant type icon display, review the images and input that section of the report. The heads-up display we refer to as a virtual windshield 406 (analogous to a 'heads-up' display in an aircraft) which could be called at any time during the examination process and would display on a single virtual windshield items relevant to the patient's entire case and/or the particular item being examined on the medical institution's checklist. During the course of a review of a virtual volumetric medical image, invoking a virtual windscreen could assist the medical person conducting the review. Questions relevant to the review could include: what is next on the checklist; what was the impetus for obtaining medical images; is there prior history of current condition; what are any laboratory results; and, if artificial intelligence routines have been applied, what were the results and any listed indictors. In this figure, an example virtual windshield 406 is shown. An example checklist with some items having been examined and others remaining. Age, gender, current condition, and any relevant medical history pertaining to current condition. Results, if any, from application of AI routines and indicators of condition. Pathology, imaging and laboratory result data are also shown, if any. Note that other items may be of interest to the person conducting the examination and those shown in this figure are examples. Also note that having all relevant information on a virtual windshield 406 can save medical person's time since the person would not have to go from the radiology PACS system to the electronic medical records system—critical information is all there and can be brought into the display at any time at the command of the person conducting the examination.

Figure 5:
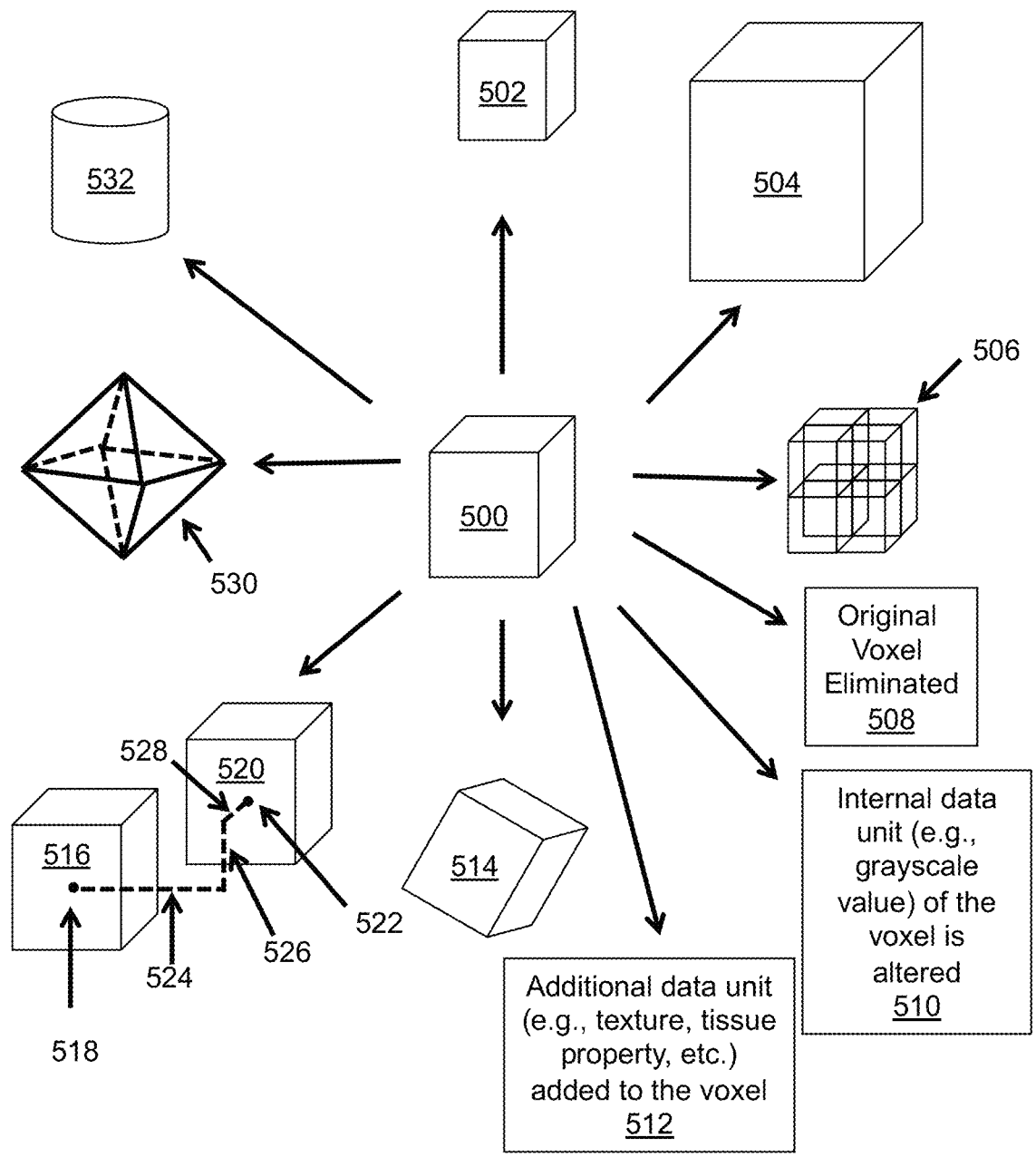
FIG. 5 illustrates flow diagram and illustration of virtual tool kit inputs leading to voxel alterations.

FIG. 5 illustrates flow diagram and illustration of virtual tool kit inputs leading to voxel alterations. Note that voxels can be manipulated in size, shape, position, orientation, or internal parameter. Further, voxels can be created or eliminated at the direction of the virtual tool. The original voxel 500 is illustrated. The size of the original voxel 500 can be decreased to yield a smaller voxel 502. The size of the original voxel 500 can be increased to yield a larger voxel 504. The original cube shaped voxel 500 can be altered such that eight smaller voxels 506 are created, such that the each of the eight smaller voxels 506 have one eighth of the volume of the original voxel 500. The original voxel 500 can also be eliminated 508. The internal data unit (e.g., grayscale value) of the original voxel 500 can be altered 510. Additional internal data units (e.g., texture, tissue type property, etc.) can be added 512. The orientation of the original voxel can be changed 514. The location of the original voxel 516 can be shifted (i.e., the voxel is moved), which can be performed by altering the x, y, z coordinate 518 of the original voxel 516 to a new x, y, z coordinate 522 of the shifted voxel 520 such that it has been moved a particular x-distance 524, y-distance 526 and z-distance 528. The shape of the original voxel 500 can change, for example changing from a cube to an octahedron 530 or to that of a cylinder 532.

Figure 6A:
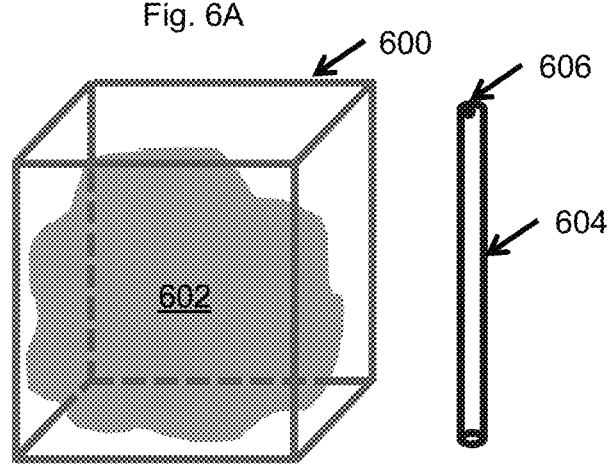
FIG. 6A illustrates a 3D cursor containing a three-dimensional image volume.

FIG. 6A illustrates a 3D cursor containing a three-dimensional image volume. A 3D cursor 600 containing a volume of interest 602 is shown. Note that the volume of interest is of homogeneous mid-gray color. Also, note that the tip 604 of the virtual tool (i.e., in this case, the virtual focal point pen) 606 is located outside of the volume of interest 604.

Figure 6B:
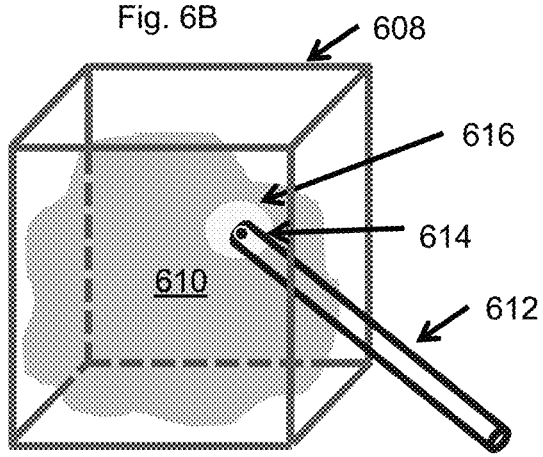
FIG. 6B illustrates manipulation of a three-dimensional image volume based on interaction with a virtual tool.

FIG. 6B illustrates manipulation of a three-dimensional image volume based on interaction with a virtual tool. 3D cursor 608 contains a volume of interest 610. A change in position and orientation of the virtual tool (i.e., in this case, the focal point pen) 612 with a portion of the virtual tool including the tip of the virtual tool 614 now entering both the virtual 3D cursor 608 is shown. The volume of interest (e.g., contains selected tissue from the volumetric medical image) 610 is shown. Note that multiple voxels 616 in close proximity to the tip 614 of the virtual tool 612 have changed/highlighted to a light gray color. Also, note that the transparency of the tissue 610 within the 3D cursor 608 has changed to better visualize the tissue 616 highlighted by the virtual focal point pen 612 and the virtual focal point pen 612 itself.

Figure 6C:
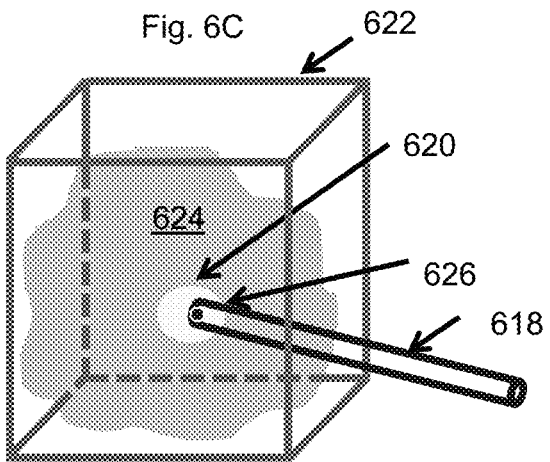
FIG. 6C illustrates manipulation of a three-dimensional image volume based on interaction with a virtual tool.

FIG. 6C illustrates manipulation of a three-dimensional image volume based on interaction with a virtual tool. The three-dimensional image volume undergoes manipulation based on interaction with a virtual tool wherein another change in position and orientation of the virtual focal point pen 618 and corresponding alterations of the visual appearance of the nearby voxels 620. A 3D cursor 622 containing a volume of interest 624 with an additional (compared to FIG. 6B) change in position and orientation of the virtual tool (i.e., in this case, the focal point pen) 618 with a portion of the virtual tool 618 including the tip of the virtual tool 626 now entering both the virtual 3D cursor 622 and the volume of interest (e.g., contains selected tissue from the volumetric medical image) 624. Note that multiple voxels 620 in close proximity to the tip 626 of the virtual tool 618 have changed/highlighted to a light gray color. Also, note that the transparency of the tissue 624 within the 3D cursor 622 has changed (compare with FIG. 6A) to better visualize the tissue 624 highlighted by the virtual focal point pen 618 and the virtual focal point pen 618 itself. This serves to assist the radiologist as to the precise location of the virtual tool within the volume of interest.

Figure 7A:
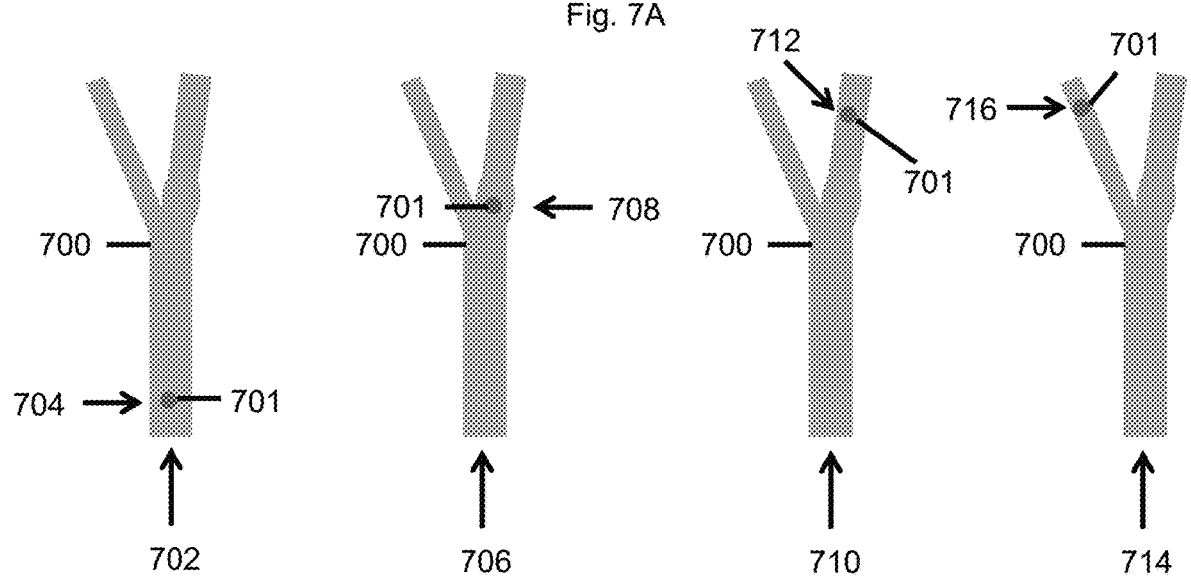
FIG. 7A illustrates virtual eye tracker symbol, which can be used with variable display patterns, such as causing the human eye to perform saccades to quickly switch from fixed object to fixed object.

FIG. 7A illustrates virtual eye tracker symbol, which can be used with variable display patterns, such as causing the human eye to perform saccades to quickly switch from fixed object to fixed object. The carotid bifurcation 700 is shown. A virtual eye tracker symbol 701 (e.g., a blue dot) at multiple positions over multiple time points. At the first time point 702, the virtual eye tracker symbol 701 is located over the inferior aspect of the common carotid artery 704 portion of the carotid bifurcation 700. At the second time point 706, the virtual eye tracker symbol 701 is located over the carotid bulb 708 portion of the carotid bifurcation 700. At the third time point 710, the virtual eye tracker symbol 701 is located over the mid aspect of the internal carotid artery 712 portion of the carotid bifurcation 700. At the fourth time point 714, the virtual eye tracker symbol 701 is located over the external carotid artery 716 portion of the carotid bifurcation 700. This facilitates human eye movement as it detects motion of a new spot so that the eye can jump to each new position. Such a system could be coupled with an eye tracking system to assure that the human looked at the eye tracking symbol. The user can control the disappearance of one virtual eye tracker symbol and the appearance of another virtual eye tracker symbol by the IO device.

Figure 7B:
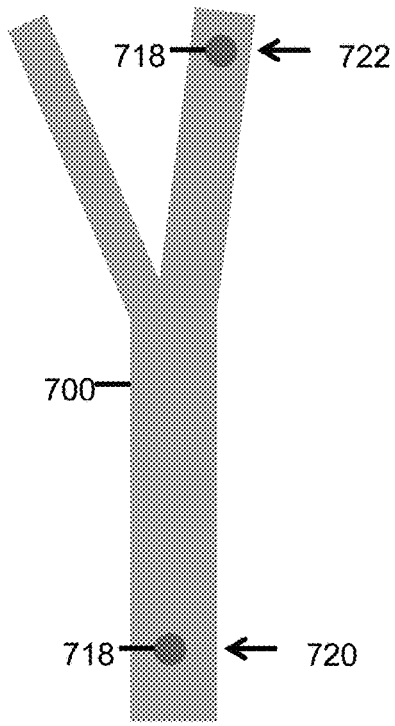
FIG. 7B illustrates the virtual eye tracker symbol.

FIG. 7B illustrates the virtual eye tracker symbol 718 located over the inferior aspect of the common carotid artery 720 portion of the carotid bifurcation 700. Over numerous time steps, the virtual eye tracker dot 718 moves in a smooth manner up to the internal carotid artery at time point #N where the virtual tracker dot 718 reaches the final destination, such as the mid portion of the internal carotid artery 722. For example, the user could select a frame rate of 60 frames per second and a movement rate of 2 cm/second. The distance that the virtual tracker dot travels would determine the total time for the particular segment. A high frame rate facilitates smooth eye tracking of the human eye and potential avoidance of skipped areas by the user leading to a more comprehensive viewing. The virtual eye tracer dot 718 can take on many shapes, sizes, colors, speed of the movement, etc.

Figure 8A:
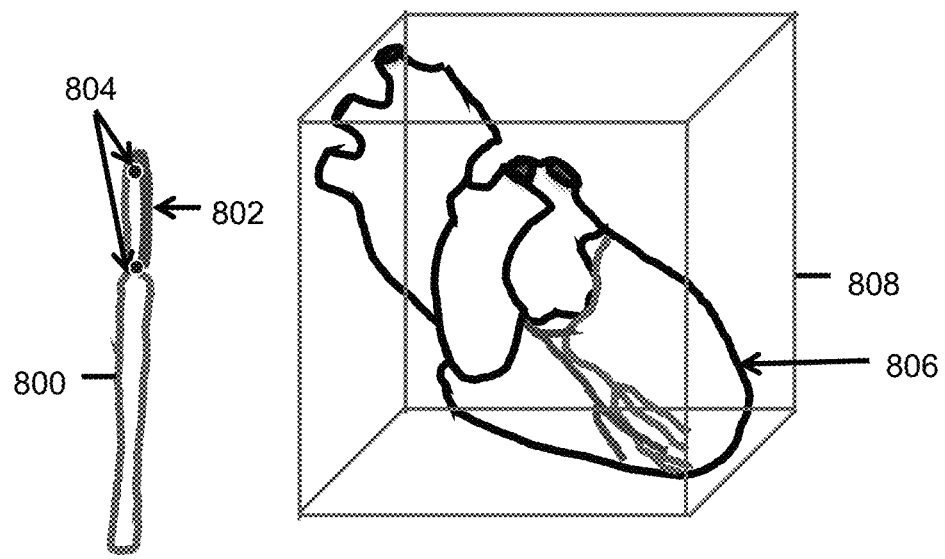
FIG. 8A illustrates the virtual knife, which can be used by medical personnel to 'carve away tissue' from an existing 3D medical imaging volume to permit enhanced viewing of the interior structure.

FIG. 8A illustrates the virtual knife 800, which can be used by medical personnel to 'carve away tissue' from an existing 3D medical imaging volume to permit enhanced viewing of the interior structure. In this example, the virtual knife 800 is used to investigate the patient's heart 806. This task is performed in conjunction with a 3D cursor 808 encasing a 3D medical volume of the heart 806. The virtual knife 800 with a virtual cutting surface 802 and associated registration point(s) 804 are shown. The medical person viewing the medical images could: pick up the virtual knife 800 and move it to the volume of interest shown as heart 806 encased in a 3D cursor 808 with tissue external to the heart subtracted.

Figure 8B:
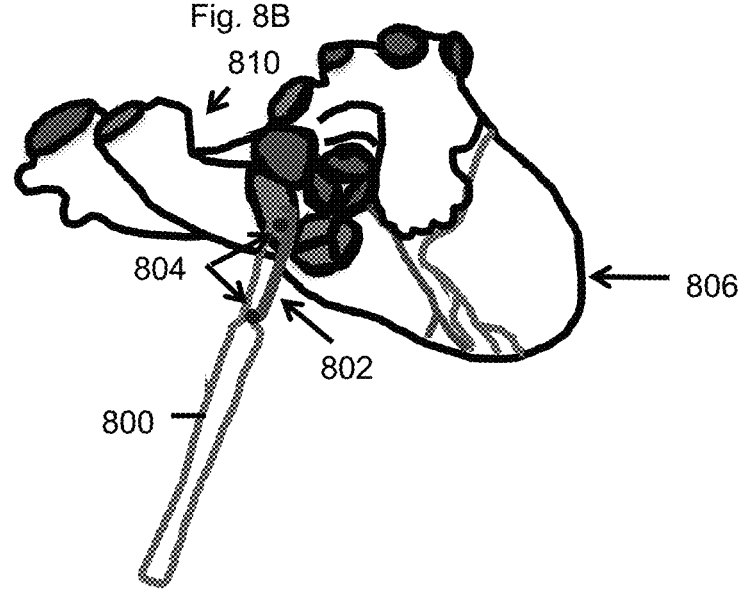
FIG. 8B illustrates passing the virtual knife equipped with a cutting surface and registration points through the 3D volume of interest such that a portion of the tissue (i.e., aorta and pulmonary artery) is cut and then displaced.

FIG. 8B illustrates passing the knife 800 equipped with a cutting surface 802 and registration points 804 through the 3D volume of interest 806 such that a portion of the tissue 810 (i.e., aorta and pulmonary artery) is cut and then displaced.

Figure 8C:
FIG. 8C illustrates removal of the aorta and pulmonary artery to allow the medical personnel to peer into the aortic valve and pulmonary valve.

FIG. 8C illustrates removal of the aorta and pulmonary artery to allow the medical personnel to peer into the aortic valve 812 and pulmonary valve 814. Further carving could allow inspection of the tricuspid valve (not shown). Finally, 4D datasets can be viewed in conjunction with the virtual tool kit to provide even more enhanced viewing of the heart.

FIG. 9A illustrates a virtual ride thru virtual blood vessel using a visual transport tool at a first position. The virtual transport tool is a means/pathway by which the medical personnel can move within a hollow structure and visualize the conditions therein. The virtual transport tool can be used alone or in conjunction with the virtual catheter. The virtual transport tool could be used in conjunction with the virtual catheter to producing a 3D digital image of the interior of the vascular structure within the patient or to train the interventionalist to treat vascular conditions. The virtual transport tool provides a vision of what is ahead within the blood vessels. In this example, a blood vessel is shown. Blood within the blood vessel could be digitally subtracted and a virtual light could shine on the blood vessel walls for some distance forward from the current viewing perspective within the tunnel and X, Y, Z coordinates of the constrictor be recorded. Note that during the segmentation process, blood would be removed from the blood vessels, but the blood vessel structure would remain. This allows the virtual transport tool to visualize the internal structure of the blood vessel unobscured. Typically, the virtual transport tool will be within the center of the blood vessel and looking ahead. Note that the center of the viewing point is within the center of the blood vessel, but the actual viewing perspectives would be offset in accordance with the left and right eye viewing perspectives. The medical person viewing the medical images could visualize what it looks like to travel within a blood vessel, as viewed from a 3D headset (e.g., augmented reality). Note that it is possible to expand the diameter of the virtual blood vessel to enhance viewing in accordance with voxel manipulations (U.S. patent application Ser. No. 16/195,251, which is incorporated by reference). As an analogy, it may be difficult to look into a small pipe or difficult to simultaneously view all portions of a large tunnel from within; therefore, the ability to adjust the size of the tunnel offers great viewing flexibility. If the user identifies an anomalous condition, then the user could take a differing position and orientation to study the condition. The distance of the blood vessel displayed would be selected by the medical personnel and the lighting intensity of the structure would also be selected by the medical personnel. A common clinical application anticipated through the use of these techniques includes measurement of a carotid atherosclerotic plaque (e.g., measuring the lumen at the narrowed regions as well as the length of the narrowing, which may prove to be a better metric for determining stent type and placement than current methods, such as the North American Symptomatic Carotid Endarterectomy Trial (NASCET) measurement technique). As an example, a small volume within the lumen over a specified length would be a better indicator for disease state and intervention as compared to current methods. A rolling computation of the lumen of each vessel would be performed with metrics provided to the medical professional. For example, this ride could be used during an assessment of the vascular structure and potential need for insertion of stents. At any time, the medical person viewing the medical images could view the vascular structure as a whole with current location of the ride in the blood vessel shown via the icon. A normal blood vessel interior surface with blood deleted 900 without plaque is shown. This largest circle 900 represents the inner aspect of the blood vessel at the current viewing location. The texture of the inner mucosal surface 901 is shown. The middle sized square dot circle 902 represents the inner aspect of the blood vessel at an intermediate distance from the current viewing location, such as 5 cm from the current viewing location. The smallest round dot circle 904 represents the farthest distance that the user could see from the current viewing location. A virtual marker, for example, the double-headed arrow 906 could indicate the length within the blood vessel actively being viewed, such as 10 cm from the current position of the blood vessel 900 to the farthest position within the blood vessel that can be seen 904. A virtual road sign 908 with distance to key intersection, such as "30.0 cm to brachiocephalic artery".

FIG. 9B illustrates a virtual ride thru virtual blood vessel using a visual transport tool at a second position. A narrowing of the blood vessel lumen due to atherosclerotic plaque and a road sign providing a description of a measurement. This largest circle 910 represents the inner aspect of the blood vessel at the current viewing location. The texture of the inner mucosal surface 911 is shown. The middle sized square dot circle 912 represents the inner aspect of the blood vessel at an intermediate distance from the current viewing location, such as 5 cm from the current viewing location. Note that a portion of the middle circle 912 at the 2 o'clock location is shown to bulge inward 916. Both the round portion of the middle circle 912 and the portion of the middle circle that bulges inward 916 are located at 5 cm from the current viewing location. Thus, the entirety of the dotted line including 912 and 916 is located at 5 cm from the current viewing location; thus, it represents an "isodistance line". The smallest round dot circle 914 represents the farthest distance that the user could see from the current viewing location, such as 10 cm from the current viewing location. A virtual marker, for example, the large double-headed arrow 918 could indicate the length within the blood vessel actively being viewed, such as 10 cm from the current position of the blood vessel 910 to the farthest position within the blood vessel that can be seen 914. A smaller double-headed arrow 920 is shown from the expected position of the dotted line (demarcating the 5 cm distance away assuming no plaque/narrowing) to the actual position that is 5 cm away and is more inwardly located 916. Please note that when the radius of a particular "isodistance line" decreases, this would indicate an area of narrowing. Please note that when the radius of a particular "isodense line" increases, this would indicate an area of expansion/ectasia/aneurysm. Also, note another virtual road sign 920 stating "5.0 cm away from a 30% atherosclerotic narrowing centered at 2 o'clock". The clock system is one example of how the location of the narrowing can be described.

FIG. 9C illustrates a virtual ride thru virtual blood vessel using a visual transport tool at a third position. The visual transport tool approaching a branching juncture of three blood vessels. During pre-panning, the medical professional could select which of the blood vessels the catheter should enter and this blood vessel could be highlighted in false color for verification of the correct path for the catheter. The largest circle 922 represents the inner aspect of the blood vessel at the current viewing location. The texture of the inner mucosal surface 923 is shown. A medium sized half circle at the 3 o'clock position 924 represents a branch vessel (e.g., internal carotid artery), which would be the desired option to travel into. A medium sized half circle at the 9 o'clock position 926 represents an additional branch vessel (e.g., external carotid artery) would be a second option to travel into, but not desired in this example scenario. A dotted red line 928 is illustrated as an example of a virtual tool to be displayed over the image as a visual cue to help notify the medical personnel of the branch that they are desiring to enter. A virtual road sign 930 is illustrated, which states "5.0 cm away from the carotid bifurcation. Head towards 3 o'clock to enter the internal carotid artery."

FIG. 10A illustrates the virtual catheter, which could be used in conjunction with a volumetric medical image of the vascular structure within the patient with the assistance of virtual icons. For example, the 3D virtual catheter could be used during pre-operative planning of an interventional operation, such as acquiring important distance or angle measurements. In this figure, an interventional procedure a 3D virtual catheter is used in treatment of an aneurysm. The solid blue line 1000 as the catheter located in the right groin region entering at the common femoral artery and extending into the right external iliac artery and to the aorta. The tip of the catheter 1002 is a small black solid circle. Note that path that has been traversed is shown as a solid lines and the planned path is shown in hashed line 1004. The planned routes can be implemented via placement of location markers in a particular blood vessel that the medical professional wants to target. Such location markers can be at way points along the desired paths or at the final target lesion 1006 (e.g., brain aneurysm). After these location markers are placed, the path connecting the markers can be marked (e.g., blue dotted line). Then measurements along the blue dotted line can be performed. With measurements, a road sign 1008 can be displayed to inform medical personnel of the distance to the vascular junction to be used in an actual interventional medical procedure. Please note that a virtual icon 1010 is also shown, such as a 2D or 3D object.

FIG. 10B illustrates the virtual catheter could be used in conjunction with a volumetric medical image of the vascular structure within the patient with the assistance of virtual icons wherein the virtual catheter is at a second position. The virtual catheter 1012 extending into the thoracic aorta. As shown, the dashed line 1016 represents the desired pathway of the catheter, which is through the brachiocephalic artery, then the common carotid artery, then the internal carotid artery then the middle cerebral artery, and finally into the aneurysm 1018. A road sign can be displayed to inform the medical personnel of the distance to the vascular junction to be used in an actual interventional medical procedure. Augmented reality distance markers could be added to the 3D virtual catheter for each intersection the interventionalist would need to take care and be prepared to change from one blood vessel to another. Screen captures of all key vascular junctures could be annotated angular changes from current path in coordinate system X-Y, X-Z and Y-Z planes.

FIG. 10C illustrates the virtual catheter in relation to a vascular structure. A blow-up view of a vascular junction wherein multiple path options occur and the medical personnel must take care in moving the catheter to the correct blood vessel. The descending thoracic aorta 1022, brachiocephalic artery 1024, left common carotid artery 1026, left subclavian artery 1028 and ascending thoracic aorta 1030 are shown. The virtual catheter 1032 is shown. The tip of the virtual catheter 1034 is shown. The blue dotted line 1036 represents the desired catheter path.

Figure 11A:
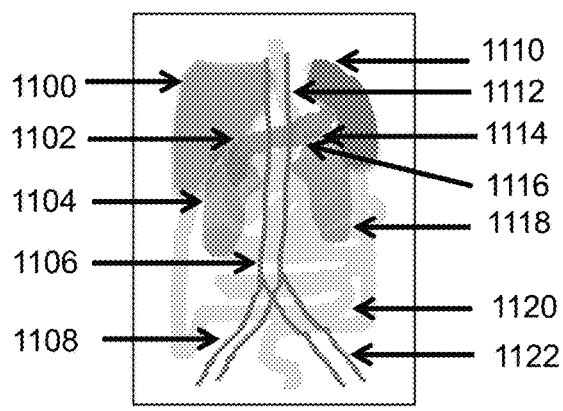
FIG. 11A illustrates a three-dimensional image volume.

FIG. 11A illustrates a three-dimensional image volume. The general concept of 3D medical images and example techniques behind the explosion of 3D medical images into multi separate organs is taught. The medical person viewing the medical images (e.g., using segmentation techniques outlined in U.S. patent application Ser. No. 15/904,092, which is incorporated by reference) could divide the 3D digital volume of interest into multiple parts based on their common characteristics (e.g., similar Hounsfeld units, anatomical atlas, etc.). The general process is illustrated in this figure wherein the desire is to examine key organs individually. Such a process could be structured, for example, in accordance with items on an image review checklist. Note illustration of organs within the abdomen. The liver 1100, right adrenal gland 1102, right kidney 1104, inferior vena cava 1106, right iliac vein 1108, spleen 1110, aorta 1112, pancreas 1114, left adrenal gland 1116, left kidney 1118, gastrointestinal tract 1120 and left iliac artery 1122 are shown. The process would be to expand these organs outward in X, Y, Z directions from an approximate center point in the torso to facilitate the individual inspection without visual interference from adjacent organs.

Figure 11B:
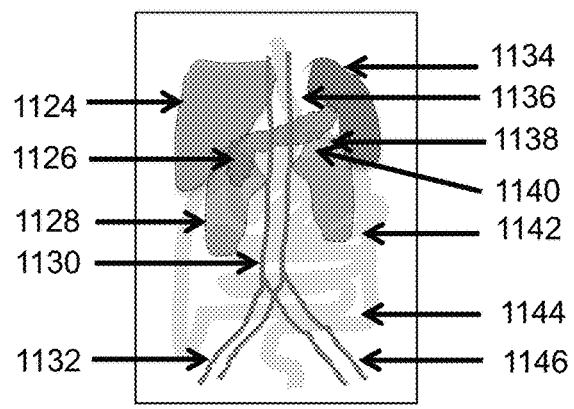
FIG. 11B illustrates segmentation of the three-dimensional image volume.

FIG. 11B illustrates segmentation of the three-dimensional image volume. Note the organs after segmentation has been applied, noting dashed lines around the organs to illustrate the segmentation process. The liver 1124, right adrenal gland 1126, right kidney 1128, inferior vena cava 1130, right iliac vein 1132, spleen 1134, aorta 1136, pancreas 1138, left adrenal gland 1140, left kidney 1142, gastrointestinal tract 1144 and left iliac artery 1146 are shown. Note that a dashed line is shown to better show the segmentation.

Figure 11D:
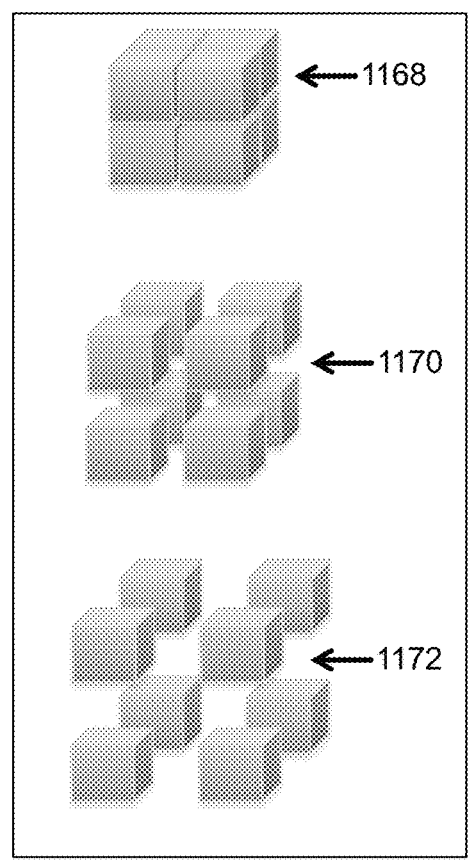
FIG. 11D illustrates one of multiple ways the sub-volumes of the 3D digital can be separated as if an explosion occurred.
Figure 11C:
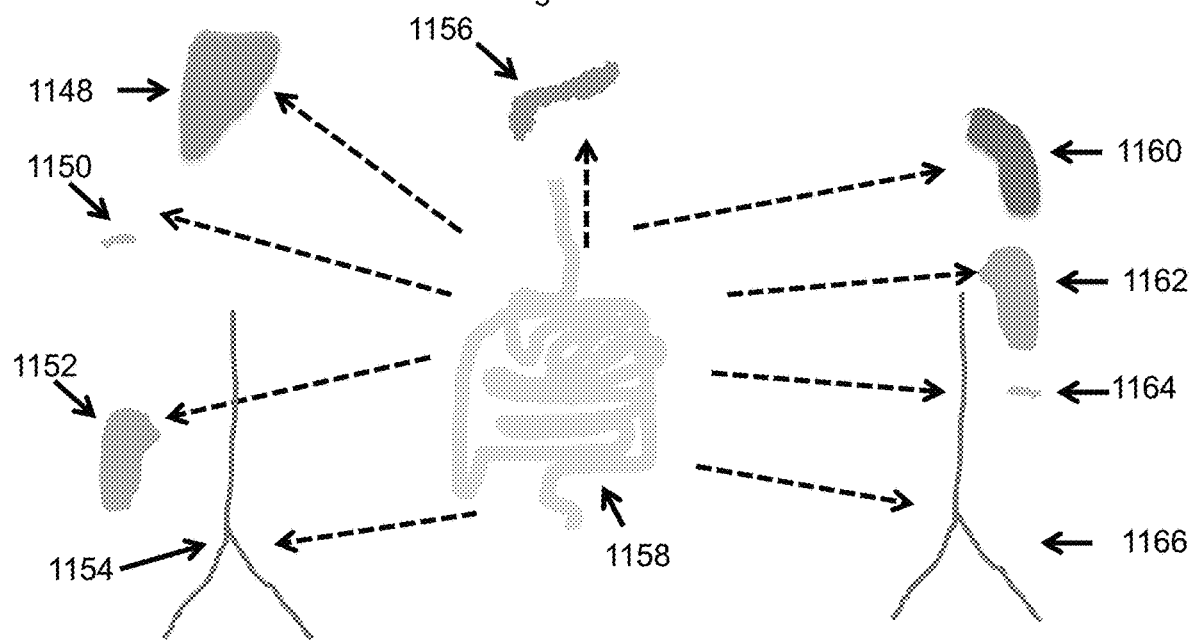
FIG. 11C illustrates an explosion of 3D medical images into multi separate organs.

FIG. 11C illustrates an explosion of 3D medical images into multi separate organs. The coordinates (X, Y, Z) of the organs would be modified to new positions indicated by the dashed lines. The software for implementation of the concept is, but not limited to, the following procedures. The medical person viewing the medical images could select a point within the 3D digital volume (ideally near the center of the 3D digital volume and between segmented subvolumes), which would act at the origin point for the explosion. The liver 1148, right adrenal gland 1150, right kidney 1152, inferior vena cava and iliac veins 1154, pancreas 1156, gastrointestinal tract 1158, spleen 1160, left kidney 1162, left adrenal gland 1164 and aorta and iliac arteries 1166 are shown.

FIG. 11D illustrates one of multiple ways the sub-volumes of the 3D digital can be separated as if an explosion occurred. One of the ways, but not limited to, is as follows: create eight large cubes 1168 each touching the center point and each parallel to the X, Y, Z axes (e.g., the first cube would be positive in X, positive in Y and positive in Z; the second cube could be positive in X, negative in Y and positive in Z; and so on). Then the medical person viewing the medical images establishes a distance factor for sub-volumes close to the center point, a larger distance factor for those further away. Then these factors are applied to all voxels within each specific sub-volume of the 3D digital image based on which cube the center voxel of the sub-volume was in. (Note that for the first cube mentioned above, for all sub-volumes whose center voxel fell in this cube the X, Y, Z coordinates of voxels within that sub-volume would increase by the specified factor in the positive X, positive Y and positive Z direction. For sub-volumes in the second cube the increases would be in positive X, negative Y and positive Z directions). The medical person viewing the medical images modify the factors changing the spread between the sub-volumes during the course of the examination. For example, a moderate spread is shown 1170. Alternatively, a larger spread is shown 1172.

FIG. 12A illustrates use of virtual transport viewer at a first position to perform a more accurate virtual colonography review. There is a tendency among the general populace to avoid having a colonoscopy due to unpleasant preparation (e.g., large volume of liquid to drink) and uncomfortable period during the procedure. One of the alternatives is to go through a virtual colonography, wherein a CT scan is performed and the inner mucosal surfaces of the colon is reviewed. If no polyps are found, a treatment phase is not necessary. If, however, polyps are found, then at some later date, the preparation phase is repeated and a treatment phase (i.e., colonoscopy) is performed to remove the polyps. In this figure the virtual transport viewer is employed to view the inside of the colon and determine if polyps are present. If none are present, all is fine and a preparation for colonoscopy is not needed. If polyps are present, they can be detected by the virtual transport viewer and, then the required preparation and subsequent treatment can be pursued. Under the virtual transport viewer process, the patient would follow a process in which he/she would: first receive a CT scan of the colon; a 3D volume of the colon would be created from the CT 2D slices (U.S. Pat. No. 8,384,771, which is incorporated by reference); segmentation (U.S. patent application Ser. No. 15/904,092, which is incorporated by reference) would identify the colon and subtraction would extract the contents of the colon (e.g., air, excrement). In so doing the colon would maintain its original shape; then the virtual transport could be inserted and enable examination back and forth and side to side within the colon. This manner of examination avoids the problem of polyps being occluded by folds which can happen during insertion of the forward looking only camera. If no polyps were found, the patient could go home confident of continued good health and he/she would have avoided the unpleasantness and discomfort of the preparation phase and colonoscopy or preparation plus air insertion phase. Note the interior surface of the colon with the air and stool deleted 900 without a polyp. This largest circle 1200 represents the inner aspect of the colon at the current viewing location. The texture of the inner mucosal surface 1201 is shown. The middle sized square dot circle 902 represents the inner aspect of the colon at an intermediate distance from the current viewing location, such as 5 cm from the current viewing location. The smallest round dot circle 1204 represents the farthest distance that the user could see from the current viewing location. A virtual marker, for example, the double-headed arrow 1206 could indicate the length within the blood vessel actively being viewed, such as 10 cm from the current position of the blood vessel 1200 to the farthest position within the blood vessel that can be seen 1204. A virtual road sign 1208 with distance to key intersection, such as "20 cm to ileocecal junction".

FIG. 12B illustrates use of virtual transport viewer at a first position to perform a more accurate virtual colonography review. The view of the interior surface of the colon with the air and stool deleted 900 with three polyps. This largest circle 1210 represents the inner aspect of the colon at the current viewing location. The texture of the inner mucosal surface 1211 is shown. The middle sized square dot circle 1212 represents the inner aspect of the colon at an intermediate distance from the current viewing location, such as 5 cm from the current viewing location. The smallest round dot circle 1214 represents the farthest distance that the user could see from the current viewing location. A virtual marker, for example, the double-headed arrow 1216 could indicate the length within the blood vessel actively being viewed, such as 10 cm from the current position of the blood vessel 1210 to the farthest position within the blood vessel that can be seen 1214. A villous polyp 1218 is illustrated. A virtual road sign 1220 with distance to key landmark is shown, such as "3 cm to villous polyp at 10 o'clock". A sessile polyp 1222 is shown. A virtual road sign 1224 with distance to key landmark is shown, such as "7 cm to sessile polyp at 4 o'clock".

Figure 13:
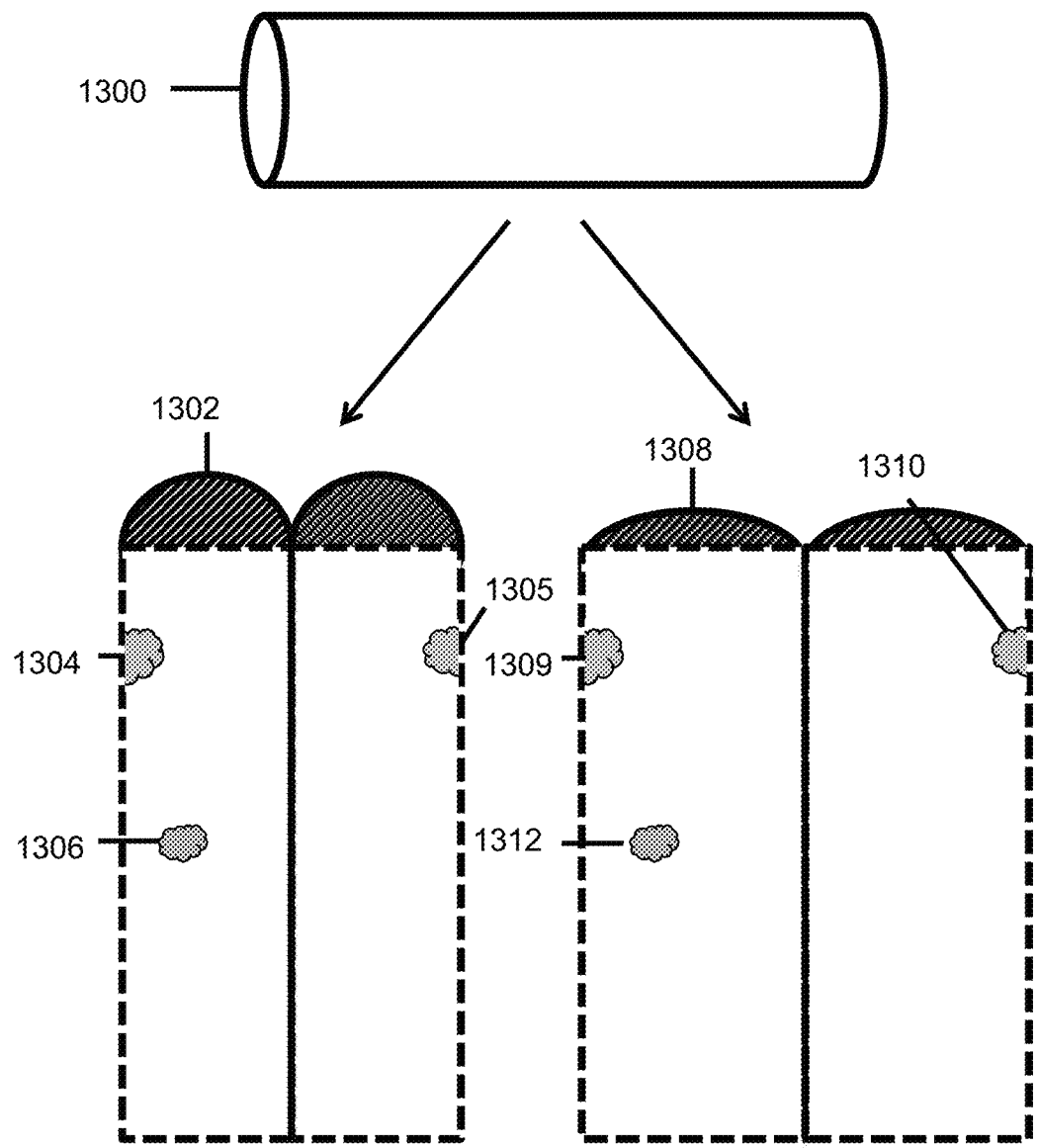
FIG. 13 illustrates a portion of a virtual 3D volumetric medical image which contains the colon portion of the large intestine which has, through voxel manipulation, been stretched in such a manner that is one long straight tube. And then, the contents within the tube have segmented and subsequently/eliminated from the tube. And, finally, the tube is split along the length axis and opened to permit viewing of the internal colon structure.

FIG. 13 illustrates a portion of a virtual 3D volumetric medical image which contains the colon portion of the large intestine which has, through voxel manipulation, been stretched in such a manner so that is one long straight tube. And then, the contents within the tube have segmented and subsequently/eliminated from the tube. And, finally, the tube is split along the length axis and opened to permit viewing of the internal structure. There are methods to physically examine the internal structure of the colon which involve: preparation, insertion of air to fill and expand the colon, insertion of a camera with light and movement of this system along the length of the colon to observe and record the internal structure. Subsequently, a rendered TV recording can be presented to medical personnel and patient. A limitation of the rendered TV recording is that polyps can be occluded from the TV view by folds along the colon. Further, if polyps are found, the patient must return at a later date for a colonoscopy which entails another preparation and subsequent removal of polyp tissue. The process invoked in this virtual process does not require the unpleasant preparation phase in the preliminary examination. In this process a CT image with/without contrast is performed. Then a 3D virtual image is constructed from the CT 2D slices (U.S. Pat. No. 8,384,771, which is incorporated by reference). Segmentation (U.S. patent application Ser. No. 15/904,092) is performed and tissue subtracted external to the colon. Also, the non-tissue contents within the colon are subtracted. Then the colon is 'stretched' so that folds which can obscure polyps are elongated and, thereby, obscuration of polyps by folded colon tissue is eliminated. This stretching process involves voxel manipulation as described in U.S. patent application Ser. No. 16/195,251. This elongated, straight virtual colon is split in 2 along the length axis so that the internal structure can be viewed via the head display unit as illustrated in this figure. The hollow viscus colon 1300 is straightened. After straightening, the colon can be opened up like a book 1302 and viewed from the top looking inside at the mucosal surface. Once opened, a first polyp is shown cut in half with a first half 1304 and a second half 1305. A second polyp is shown intact 1306. Alternatively, the colon can be opened up like a book and pulled apart to flatten it out 1308 and viewed from the top looking inside at the mucosal surface. Once opened, a first polyp is shown cut in half with a first half 1309 and a second half 1310. A second polyp is shown intact 1312. When the colon is flattened, a polyp will pop out more with 3D viewing on a headset.

FIG. 14A illustrates insertion of virtual contrast and its flow through the vascular system at a first time point. Initially, the blood within the affected vessels has been removed. In the top row, the blood vessels are in their normal, non-pathologic state and normal blood flow is illustrated through the placement of virtual contrast. The proximal portion of the blood vessel 1400, mid portions of the blood vessel 1401a and 1401b and distal portions of the blood vessel 1402a, 1402b and 1402c are shown. Thus, when virtual contrast is inserted, it would mimic normal blood flow where it to be imaged. At the initial time point, all of the native blood voxels have been removed and no virtual contrast has been inserted.

FIG. 14B illustrates insertion of virtual contrast and its flow through the vascular system at a second time point. At the subsequent time point, some virtual contrast 1410 shown in gray has been inserted into the proximal portion of the blood vessel 1400 and mid portions of the blood vessel 1401a and 1401b, but no virtual contrast (the lack of virtual contrast is displayed in white) has been inserted into the distal portions of the blood vessel 1402a, 1402b and 1402c.

FIG. 14C illustrates insertion of virtual contrast and its flow through the vascular system at a third time point. At the third time point, virtual contrast 1412 shown in gray has been inserted into the proximal portion of the blood vessel 1400, mid portions of the blood vessel 1401a and 1401b, and distal portions of the blood vessel 1402a, 1402b and 1402c.

FIG. 14D illustrates insertion of virtual contrast and its flow through the vascular system at a first time point wherein there is a blood clot within a branch. A pathologic state (i.e., a blood clot 1413 is lodged into one of the distal artery branches) is shown. The proximal portion of the blood vessel 1400, mid portion of the blood vessel 1401a and 1401b and distal portions of the blood vessel 1402a,1402b and 1402c are again shown. Thus, since a blood clot 1413 is present, when virtual contrast is inserted, the virtual contrast would mimic an altered blood flow pattern. At the initial time point, all of the native blood voxels have been removed and no virtual contrast has been inserted.

FIG. 14E illustrates insertion of virtual contrast and its flow through the vascular system at a second time point wherein there is a blood clot within a branch. At the second time point, some virtual contrast 1410 shown in gray has been inserted into the proximal portion of the blood vessel 1400 and mid portions of the blood vessel 1401a and 1401b, but no virtual contrast (the lack of virtual contrast is displayed in white) has been inserted into the distal portions of the blood vessel 1402a, 1402b and 1402c.

FIG. 14F illustrates insertion of virtual contrast and its flow through the vascular system at a third time point wherein there is a blood clot within a branch. At the third time point, virtual contrast 1412 shown in gray has been inserted into the proximal portion of the blood vessel 1400, mid portions of the blood vessel 1401a and 1401b, and two of the distal branches of the blood vessels 1402b and 1402c; however, one of the distal portion of the blood vessel 1402a does not fill with virtual contrast 1412 because it is blocked by a blood clot 1413. Thus, when blood clot is present, which is assigned a blockage-type interactive voxel parameter. In this illustration, insertion of virtual contrast is shown in the normal setting of a blood vessel and in the altered setting of a blood vessel (i.e., with a blood clot). Note that the virtual contrast can progress from proximal to distal up to the point of the clot, but not beyond the clot. The remaining branches experience the insertion of virtual contrast. Thus, assigning a blockage-type interactive voxel parameter stops flow of virtual contrast. Alternatively, a surgical clip blockage-type interactive voxel parameter can be used.

Figure 15A:
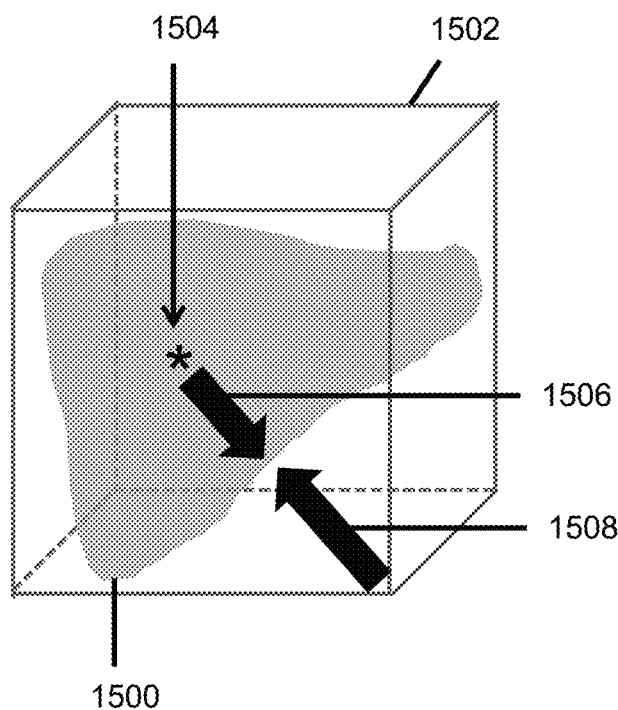
FIG. 15A illustrates an ablation technique could be used, inter alia, in conjunction with 3D digital structure within a 3D cursor.

FIG. 15A illustrates an ablation technique could be used, inter alia, in conjunction with 3D digital structure within a 3D cursor. This permits careful examination of the interior of an organ. The method underlying the ablation technique is described. The outer 'shell' of organ of interest to the medical person viewing the medical images is determined (e.g., using segmentation techniques outlined in U.S. patent application Ser. No. 15/904,092) (Note: in this figure a liver 1500 is illustrated which is encased in a 3D cursor 1502 (U.S. Pat. No. 9,980,691). To determine the outer shell of the liver, one could proceed from the center voxel 1504 within the 3D cursor in an outward direction 1506 to the segmented surface of liver tissue. Alternatively, one could proceed in an inward direction 1508 from the 3D cursor sides until such distance reaches the segmented surface of liver tissue. This process permits the tissue external to the liver to be subtracted.)

Figure 15B:
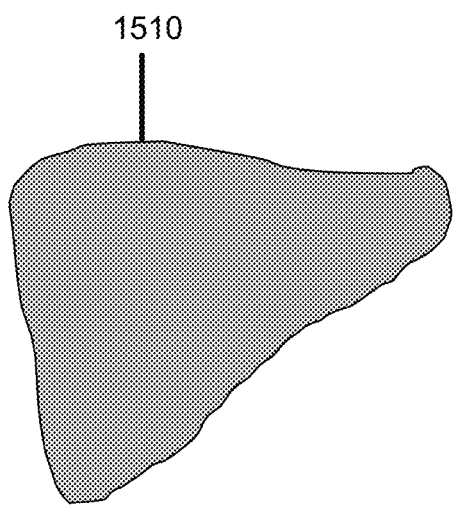
FIG. 15B illustrates the next step of the process which is sequentially eliminate one voxel deep from all of the voxels on the outer surface.

FIG. 15B illustrates the next step of the process which is sequentially eliminate one voxel deep from all of the voxels on the outer surface. For example, the outer shell of voxels is shown in black 1510. Then, repeat this step multiple times on the remaining outer layer(s) of tissue at the direction of the medical person viewing the medical images. Alternatively, select one layer in the X, Y, Z coordinate system (e.g., select the X—Y layer with the highest Z coordinate and eliminate that layer—repeat this step multiple times on the remaining 3D digital volume at the direction of the medical person viewing the medical images.

Figure 15C:
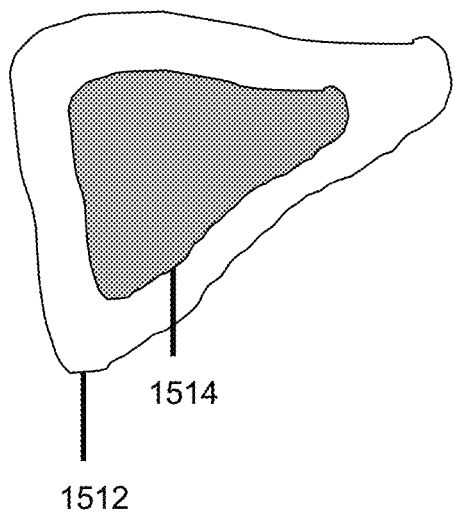
FIG. 15C illustrates the next step of the process, which is as the layers are subtracted, the internal tissue types are revealed.

FIG. 15C illustrates the next step of the process, which is as the layers are subtracted, the internal tissue types are revealed. The original outer shell 1512 is shown. The shell after N steps of the ablation 1514 is shown. Note that methods by which to display voxels may include sparse display or translucent appearance of non-prioritized voxels whereas voxels that are prioritized would not be sparsely displayed.

Figure 15D:
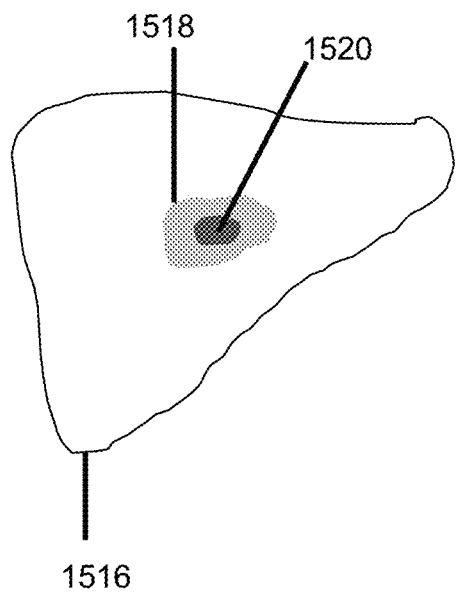
FIG. 15D illustrates normal liver tissue is ablated away and abnormal liver tissue remains.

FIG. 15D illustrates normal liver tissue is ablated away and abnormal liver tissue remains. Note that the original outer shell 1516 is shown. In this example, a benign lesion called focal nodular hyperplasia 1518 is revealed after the ablation process. The focal nodular hyperplasia 1518 is shown with the characteristic imaging feature of the hypoattenuating central scar 1520. Such a process would be a more useful method for viewing of tumors inside of a solid organ as compared to the process of searching on each slice. Note that the volume of liver tissue has decrease from the original volume as a result of repeated ablative steps.

Figure 16:
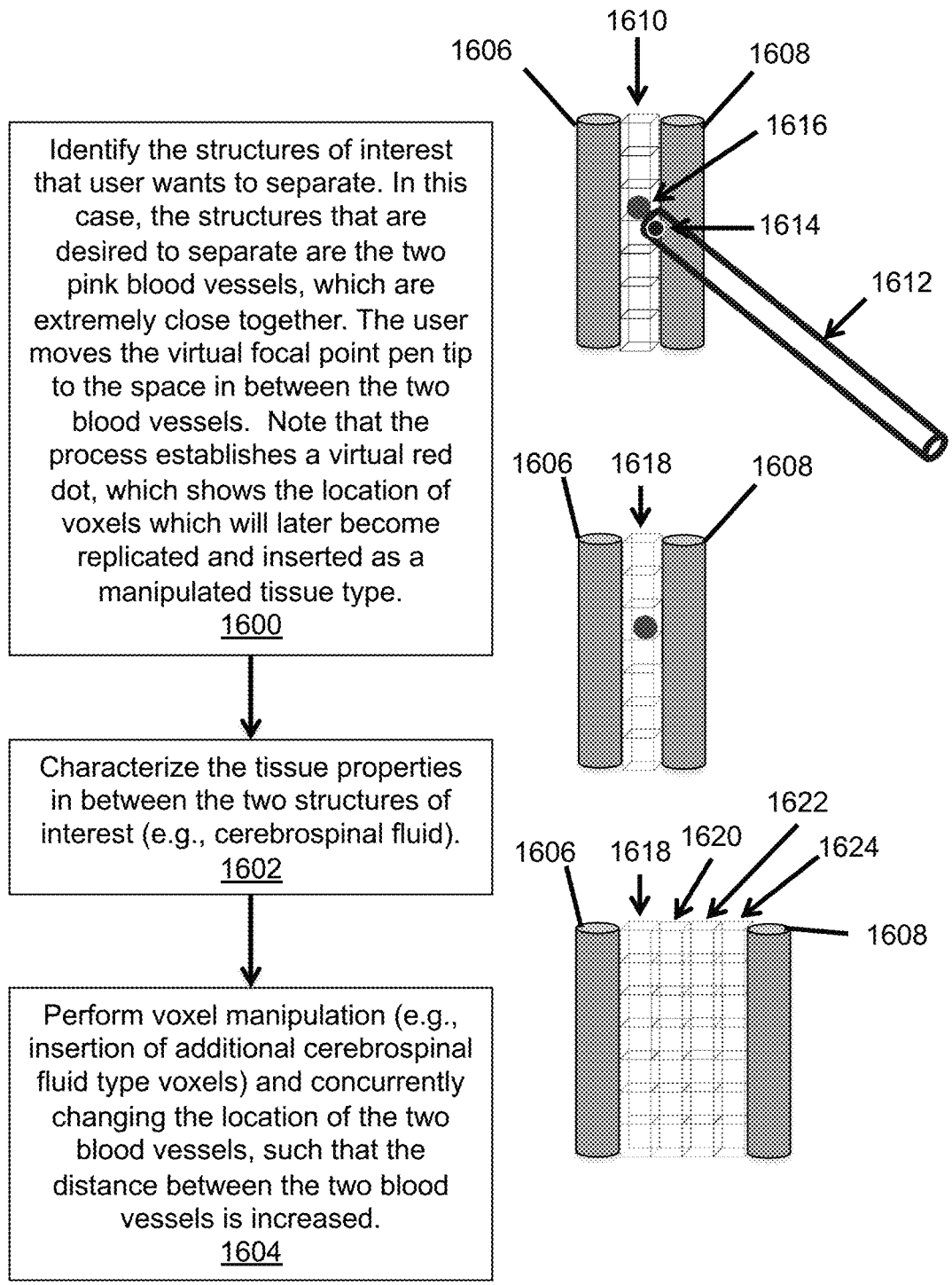
FIG. 16 illustrates virtual focal point pen guiding voxel manipulation.

FIG. 16 illustrates a virtual focal point pen guiding voxel manipulation. The movement of the virtual focal point pen would be controlled by medical person viewing the medical images. This figure illustrates expanding distance between blood vessels which are closely space, overlapping and difficult to differentiate and a process to expand the distance between blood vessels. If an arteriovenous malformation occurs in the brain in a region where multiple blood vessels are close together, it is difficult to identify which of these blood vessels to inject treatment material. Expanding the distance digitally can help identify the proper blood vessel for injection. Two conditions will be discussed. First, non-blood vessel tissue separates the blood vessels. Second, several blood vessels are in a cluster with little or no non-blood vessel tissue separating the blood vessels. If different types of tissue separate the blood vessels, then: a) segmentation to determine types of tissue present in the volume of interest; b) for all non-blood and non-blood vessel type of tissue, expand the volume by a multiplicative or additive factor; c) adjust the coordinates of blood and blood vessels to account for the expansion of the non-blood and non-blood vessel type of tissue. Next, to illustrate the cluster: d) perform segmentation to determine which voxels are predominately blood and which voxels are tissue (i.e., blood vessels); e) temporarily eliminate the tissue voxels; c) then use a multiplicative (or additive factor) to all coordinates of blood voxels; f) apply smoothing routine to blood vessels (optional); g) encase the blood voxels with tissue vessels. The display for the medical person viewing the medical images show the expanded blood vessel structure and thereby facilitate treatment. One of the problems encountered in radiology is the difficulty understanding the relationship between multiple complex anatomical structures. An example is a cerebral arteriovenous malformation (AVM). A complex cerebral AVM can consist of multiple tortuous feeding arteries, a tangle of nidus with aneurysms and multiple draining veins. It is extremely difficult to understand the precise anatomy of this complex structure. A process is illustrated as follows. In the first step 1600, identify the structures of interest that user wants to separate. In this case, the structures that are desired to separate are the two pink blood vessels, which are extremely close together. The user moves the virtual focal point pen tip to the space in between the two blood vessels. Note that the process establishes a virtual red dot, which shows the location of voxels which will later become replicated and inserted as a manipulated tissue type. In the second step 1602, characterize the tissue properties in between the two structures of interest (e.g., cerebrospinal fluid). In the third step 1604, perform voxel manipulation (e.g., insertion of additional cerebrospinal fluid type voxels) and concurrently changing the location of the two blood vessels, such that the distance between the two blood vessels is increased. A first blood vessel 1606 and a second blood vessel 1608 are closely spaced with only a sliver of intervening cerebrospinal fluid type voxels 1610. A virtual pointer 1612 is shown. The tip of the virtual pointer 1614 is also shown. A virtual symbol (e.g., red dot 1616) is also shown to mark the location in the imaging volume that will be manipulated. Then, the tissue properties in between the two structures of interest (e.g., cerebrospinal fluid) can be assigned a particular tissue property. To illustrate this, the borders of each of these voxels has changed to a light blue 1618. Note that at this point, a first blood vessel 1606 and a second blood vessel 1608 are still closely spaced to one another. Then, to separate the first blood vessel 1606 from the second blood vessel 1608, three additional columns of cerebrospinal fluid voxels 1620, 1622 and 1624 are inserted. Note that the spacing between the first blood vessel 1606 and the second blood vessel 1608 has been increased. This is useful in that 3D viewing may now be improved with better ability to see and understand the relationship between closely spaced structures.

Figure 17:
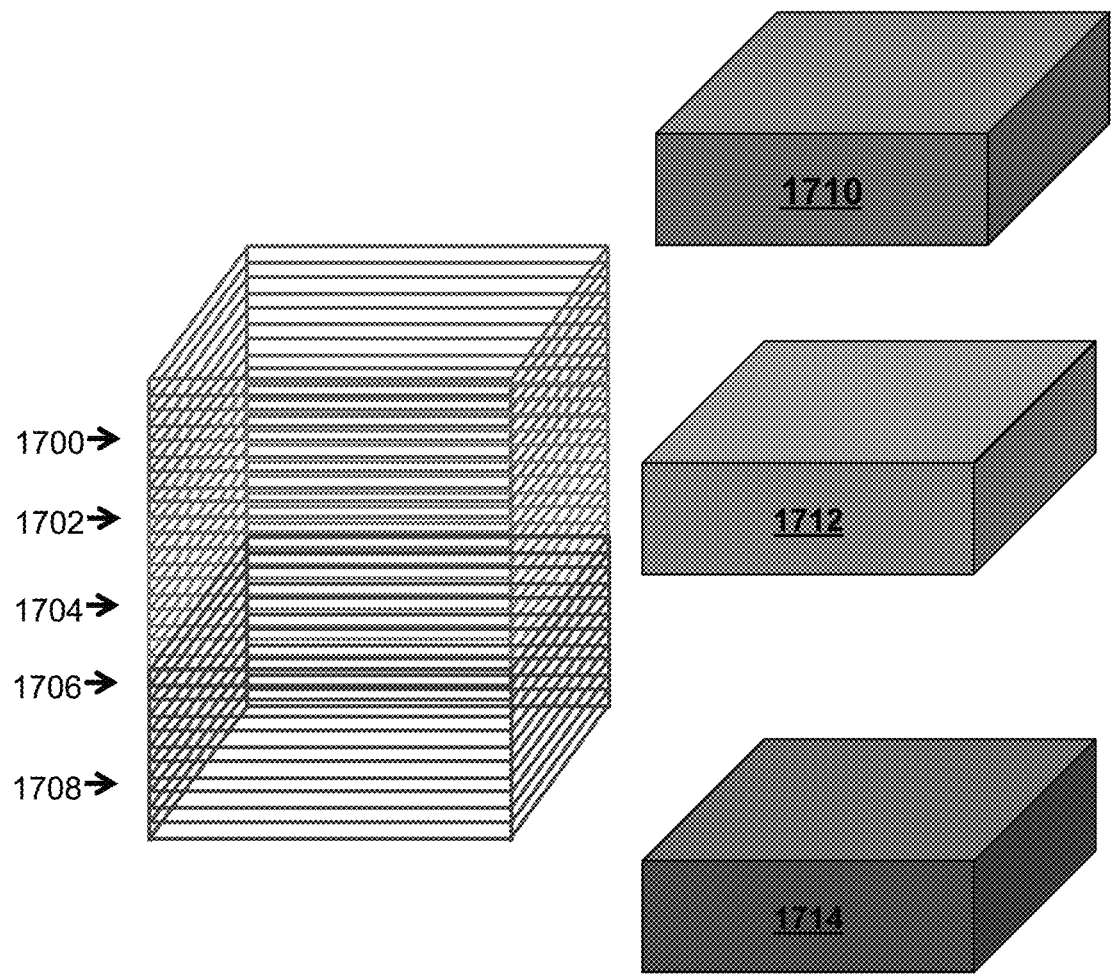
FIG. 17 illustrates the total imaging volume and multiple types of sub-volumes.

FIG. 17 illustrates the total imaging volume and multiple types of sub-volumes. In contrast to a slice-by-slice approach, which has traditionally been used in radiology, we present a sub-volume-by-sub-volume approach is displayed here. Note that slices can be arranged to build a volume as described in U.S. Pat. No. 8,384,771. A medical professional (or computer program) could first select specific spot 1700 to mark the boundary between a first set of 2D slices 1702 and a second set of 2D slices 1704. A medical professional (or computer program) could second select specific spot 1706 to mark the boundary between a second set of 2D slices 1704 and a third set of 2D slices 1708. Once the slices for a particular sub-volume are determined, the sub-volume can pulled out of the stack of 2D slices and be viewed and analyzed. In this illustration, a first sub-volume 1710 created from a first set of 2D images 1700 is pulled to upward and to the side of the first set of 2D images 1700. A second sub-volume 1712 created from a second set of 2D images 1704 is pulled to the side of the second set of 2D images 1704. A third sub-volume 1714 created from the third set of 2D images 1708 is pulled to the side and downward in relation to the third set of 2D images. Please note that multiple methods of assigning boundaries of stacks could be performed. For example, picking a convenient sub-volume size (e.g., 20 2D slices) and dividing the sub-volumes accordingly (e.g., slices 1-20 are assigned to sub-volume #1, slices 21-40 are assigned to sub-volume #2, etc.). The number of slices in each stack can vary. Alternatively, the user could use the virtual pen to touch and select the boundaries, such as points 1702 and 1706. The total imaging volume can be divided into many different combinations of sub-volumes of varying size, which can be viewed from many different angles (U.S. Pat. No. 8,384,771). In this example, sub-volumes can be made from arranging a collection of slices.

Figure 18:
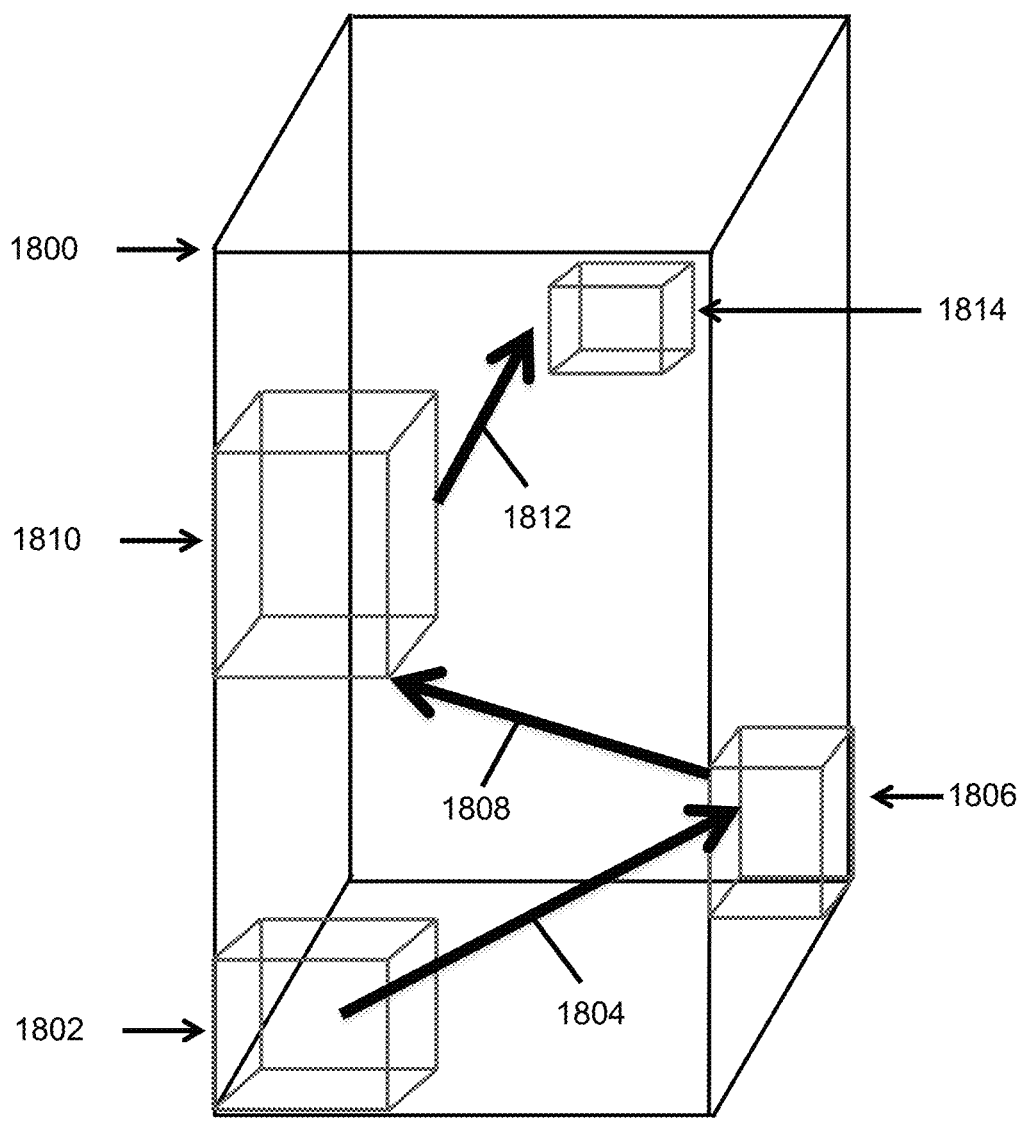
FIG. 18 illustrates sequencing of movement of the 3D cursor through the volume of interest in a random pattern.

FIG. 18 illustrates sequencing of movement of the 3D cursor through the volume of interest in a random pattern. A random pattern is used based on items of possible interest, the reviewing medical person can view the totality of the virtual medical image volume at once and apply techniques such as changing transparency and applying false color to structures of differing density than the nominal density of the organ being examined. The reviewer can then move and re-size the 3D cursor to the various objects of potential interest for detailed examination. In this illustration, a total scanned volume 1800 is shown. A first sub-volume displayed in a 3D cursor is shown at the first time point 1802. The 3D cursor is subsequently moved in direction 1804. A subsequent sub-volume displayed in a second re-sized 3D cursor is shown at a subsequent time point 1806. The 3D cursor is subsequently moved in direction 1808. A subsequent sub-volume displayed in a second re-sized 3D cursor is shown at a subsequent time point 1810. The 3D cursor is subsequently moved in direction 1812. A subsequent sub-volume displayed in a second re-sized 3D cursor is shown at a subsequent time point 1814. This figure shows multiple moves and resizes the 3D cursor to view example tissues of interest. This can type of search pattern can expedite the review process. This search patterns employ a 3D cursor (U.S. Pat. No. 9,980,691 and U.S. patent application Ser. No. 15/878,463). Note: when reviewing medical images in the original 2D format, the eyes jump from one spot to another following the reviewing individual's saccadian path and substantial portions of a slice may not be observed and, consequently, small masses may be missed. In the use of the 3D cursor, small findings subtend a larger fraction of presented image and the probability of detection increases proportionally. If such a random search pattern is displayed, the computer program would keep track of the portions of the total volume that have been displayed and the portions of the total volume that have not been displayed. In the event that some portions of the total volume have not been displayed by a 3D cursor, the program would remind the user to view these regions. In some implementations, sub-volumes are displayed to the medical personnel in an automated pattern, which includes, but is not limited to, the following: windshield wiper pattern or layer-by-layer pattern. At any time point, the 3D cursor and/or sub-volume within the 3D cursor can be copied and pasted to a virtual movable table for later review. For example, the radiologist may want to round up all of the potentially abnormal or definitely abnormal findings first. Then, the radiologist may want to study each of the abnormal findings in great detail at a later time period. Each time an abnormal imaging finding is identified, the radiologist could place the abnormal finding in a 3D cursor and make sure that the entirety of the abnormal finding is included in the sub-volume (e.g., the entirety of the liver mass is included in the 3D cursor, which defines the boundaries of the sub-volume). Then, set the sub-volume aside into a virtual bucket or virtual 3D clipboard. Then, review the rest of the total imaging volume. Once the entire total imaging volume has been removed and all abnormal sub-volumes have been placed in the virtual bucket or virtual 3D clipboard, then the radiologist would begin close inspection of the volumes in the virtual bucket or virtual 3D clipboard.

Figure 19:
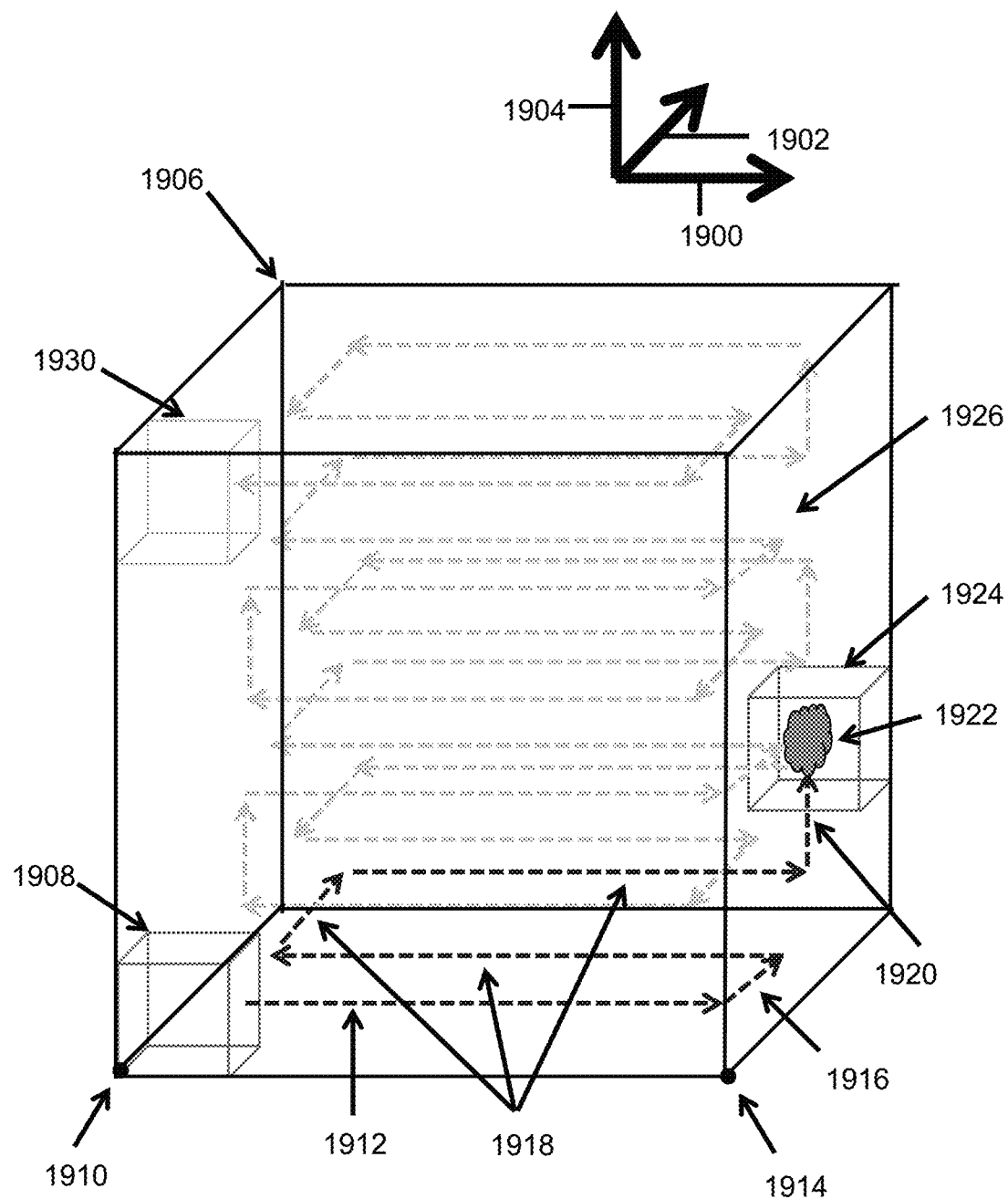
FIG. 19 illustrates an example of a systematic pattern of viewing of medical images (e.g., sequential virtual windshield wiper type pattern).

FIG. 19 illustrates an example of a systematic pattern of viewing of medical images (e.g., sequential virtual windshield wiper type pattern). The x-direction 1900, y-direction 1902 and z-direction 1904 are shown. The total imaging volume 1906 is shown. A virtual windshield wiper can have several implementations with the cursor moving in multiple systematic fashions. As illustrated, a first sub-volume 1908 being examined in the 3D cursor at the initial time point where one of the coordinates of the 3D cursor has one corner at position (0, 0, 0) 1910 is shown. The 3D cursor first moves in a fashion wherein the x-direction is increased 1912 and the y-coordinates and z-coordinates of the 3D cursor are unchanged as illustrated by the dashed arrow and the sub-volumes along this movement direction can be optimized. Thus, the pattern is to sequentially increase the X coordinate while holding the Y and Z coordinates constant. Once the corner of the 3D cursor reaches a maximum x-value of the total imaging volume 1906, then the 3D cursor is moved in a fashion wherein the y-direction is increased 1916 and the x-coordinates and z-coordinates of the 3D cursor are unchanged, as illustrated by the dashed arrow and the sub-volumes along this movement direction can be optimized. Thus, when the max value for the X coordinate is reached, the y coordinate is increased an increment and the X coordinate is sequentially decreased until the min X coordinate is reached, then Y coordinate is again incremented. This process of moving the 3D cursor in the x-direction 1900 and y-direction 1902 is then repeated 1918 until at which point a bottom layer of the total imaging volume 1906 has been fully examined by the 3D cursor. When this plain has been completed, the Z coordinate is incremented. The 3D cursor can be shifted 1920 upwards in the z-direction 1904. Note that during this systematic search pattern, an abnormality 1922 may be discovered at a particular 3D cursor position 1924. Such an abnormality can be placed in to a virtual bucket or virtual 3D virtual movable table for further analysis. Multiple additional systematic movements of the 3D cursor through the total imaging volume 1906 can be performed as illustrated 1926 until at which point the all sub-volumes within the total imaging volume have been examined and the 3D cursor reaches its final spot 1928. A variation of the windshield pattern is a 'fly back' wherein after the first row is completed, the pattern resumes with incrementing Y coordinate and then resuming incrementing the X coordinate. This type of search pattern helps ensure a thorough examination has been performed. This search patterns employ a 3D cursor (U.S. Pat. No. 9,980,691 and U.S. patent application Ser. No. 15/878,463). Note: when reviewing medical images in the original 2D format, the eyes jump from one spot to another following the reviewing individual's saccadian path and substantial portions of a slice may not be observed and, consequently, small masses may be missed. In the use of the 3D cursor, these small masses subtend a larger fraction of presented image and the probability of detection increases proportionally. In some implementations, sub-volumes are displayed to the medical personnel in an automated pattern, which includes, but is not limited to, the following: windshield wiper pattern or layer-by-layer pattern. An automated search pattern through the volume of interest may prove to increase the probability of detection. In this illustration, an automated search pattern is shown as the 3D cursor moves through the volume of interest. Note that a mass is identified in a later sub-volume. Future automated search pattern through the volume of interest is performed back and forth in each layer (similar to a windshield wiper) and then back and forth in the next layer.

Figure 20:
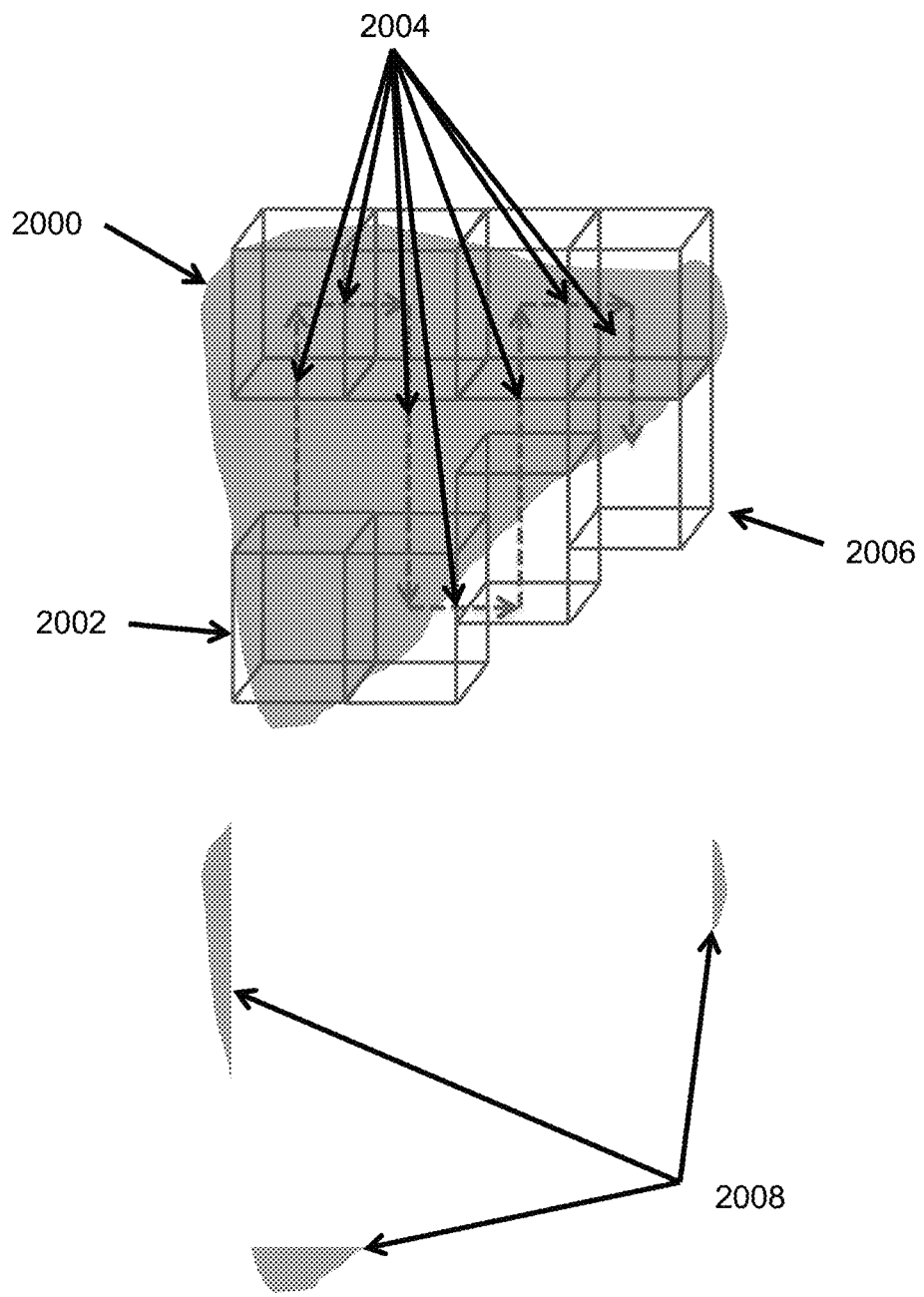
FIG. 20 illustrates volume of interest to be reviewed and a process whereby any areas which intended for review which were missed could be highlighted to the medical person performing the review. These identified sub-volumes could be reviewed subsequently, thereby ensuring completeness of the review.

FIG. 20 illustrates volume of interest to be reviewed and a process whereby any areas, which intended for review which were missed, could be highlighted to the medical person performing the review. These identified sub-volumes could be reviewed subsequently, thereby ensuring completeness of the review. This process invokes the sequential selection of sub-volumes of the volume of interest through use of the 3D cursor (U.S. Pat. No. 9,980,691 and U.S. patent application Ser. No. 15/878,463) to sequentially step through the volume being examined (e.g., per following medical institution checklist). Further, after the step-by-step process has been completed, the question could arise as to whether the entire volume has been examined. In this implementation, the volume contained in each of the 3D cursors which had been examined could be totaled and subtracted from the total original volume. This could result missing some portions of the original volume that were intended for review. In this implementation, these missed portions would be highlighted to the medical person performing the review and he/she could be alerted to continue the review and examine these missed portions. Note: when reviewing medical images in the original 2D format, the eyes jump from one spot to another following the reviewing individual's saccadian path and substantial portions of a slice may not be observed and, consequently, small masses may be missed. In the use of the 3D cursor, these small masses subtend a larger fraction of presented image and the probability of detection increases proportionally. This figure illustrates sequencing of movement of the 3D cursor through an organ of interest. A volume of interest (i.e., liver) 2000 is shown. A sub-volume 2002 displayed at time point #1 is illustrated. The 3D cursor moves 2004 in a systematic fashion through the volume of interest 2000 such as described in FIG. 19. The final sub-volume 2006 would be displayed at time point #N. Control of viewing of the medical images (e.g., changing from one increment to another) would be controlled by the medical personnel. Alternatively, the user could move the control the movement of the 3D cursor by the joystick or other geo-registered tools, as discussed in U.S. patent application Ser. No. 16/524,275. Finally, volumes displayed in the 3D cursor can be tracked and then reviewed at a later time (i.e., prior to the completion of the exam). Sub-volume size changes based on indication routine screening versus cancer. Further, recording the position of the 3D cursor over time and comparing the sub-volumes displayed with the total volume would enable accounting for sub-volumes that have not yet been displayed to the medical professional 2008. Alternatively, subtracting the sub-volumes have been displayed from the whole volume, it is possible to determine which sub-volumes have not yet been displayed. Note that a few areas of the structure were missed (i.e., not included in the 3D cursor volumes) 2008; these can be tracked and the radiologist has the option to review these areas prior to the completion of the exam. These missed sub-volumes 2008 can be moved to a new position and examined. In another embodiment, the user can select the size of the 3D cursor, rate of the movement of the cursor and the computer performs automated movement through the volume of interest on the checklist item. If the organ is unremarkable, the sub-volumes within the cubes could be changed in a way that an the imaged structures are unremarkable (e.g., deleted, changed in Hounsfield unit, etc.).

Figure 21A:
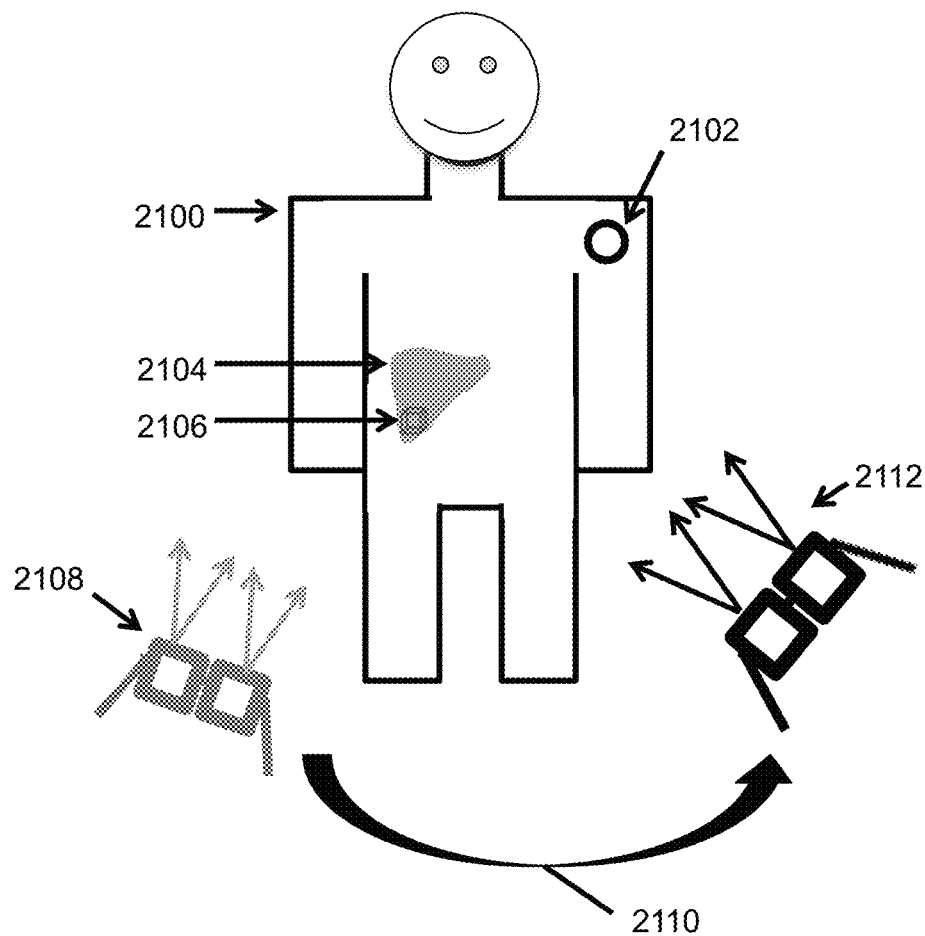
FIG. 21A illustrates an icon of a human with the location of the 3D virtual cursor included at the approximate location within the body.

FIG. 21A illustrates an icon of a human with the location of the 3D virtual cursor included at the approximate location within the body. This icon could be used in conjunction with viewing display of 3D medical images. During the course of the examination of the volume by the medical person viewing the medical images, it may be useful to quickly refer to an icon in order to re-orient where exactly in the body is some tissue of interest/concern. The icon would also be of utility in discussions between medical personnel. The icon of the body in a vertical position facing forward 2100 is shown. The icon is marked up with an outline of the sub-volume being examined. Such a markup includes, but is not limited to, the following: markup of region of area of concern as indicated by the ordering physician; markup of the segmented volume that the radiologist is actively working on (e.g., radiologist is actively working on the liver item on the checklist, so the segmented liver is marked up on the icon); markup of sub-volume being examined by the radiologist (e.g., radiologist is actively working on a sub-volume within the liver within the confines of the volume-subtending 3D cursor); markup of viewing perspectives in relation to the icon. For example, the ordering physician may indicate an area of concern (e.g., sending patient specific image to the radiologist as described in U.S. Provisional Patent Application 62/843,612 for METHOD OF CREATING A COMPUTER-GENERATED PATIENT SPECIFIC IMAGE) and this area can be marked up on the virtual icon 2102. Next, the segmented volume 2104 that the radiologist is actively working on (e.g., liver) can be marked up. Next, a sub-volume within a 3D cursor 2106 can be marked up. An additional symbol may be shown external to the icon. For example, an initial viewing perspective symbol 2108 is shown to denote the initial viewing perspective. A movement symbol 2110 to denote the change in position from the initial viewing perspective denoted by the initial viewing perspective symbol 2108 to the subsequent viewing perspective denoted by the subsequent viewing perspective symbol 2112.

Figure 21B:
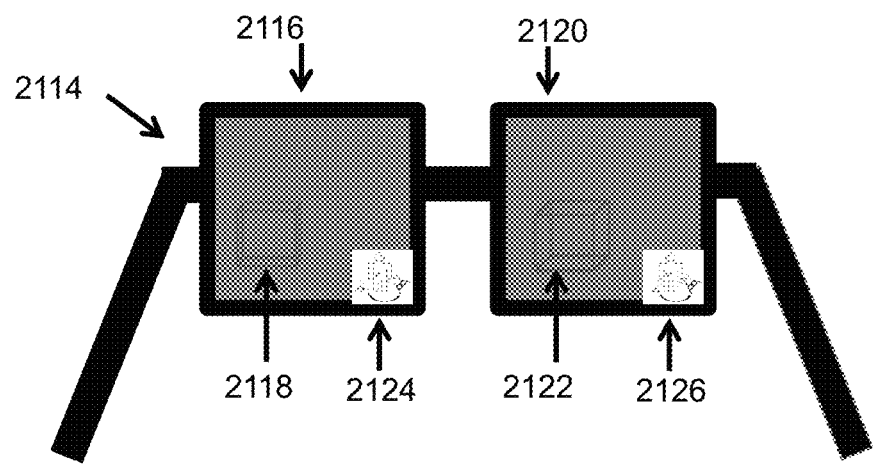
FIG. 21B illustrates the user's extended reality headset is illustrated with a left eye display showing a left eye view of the 3D cursor and icon and a right eye display showing a right eye view of the 3D cursor and icon.

FIG. 21B illustrates the user's extended reality headset 2114 is illustrated with a left eye display 2116 and a left eye view of the 3D cursor 2118 and a right eye display 2120 with a right eye view of the 3D cursor 2122. Note that a left eye view of the marked up 3D icon 2124 is shown in the left eye display 2116 and a right eye view of the marked up 3D icon 2126 is shown in the right eye display. Thus, the outline of the sub-volume being examined can be one of the markups of the icon. The approximate location of the 3D cursor(s) within the human body icon is another example markup of the icon. Orientation of the body would be under the control of the medical person viewing the medical images, as would whether to display the icon or not. For example, the icon could be rotated, translated, warped (with corresponding voxel manipulation if desired) or other alterations as directed by the radiologist. Furthermore, adding a marked up icon of a 3D cursor to the diagnostic 2D radiology monitor could be performed. As the medical person viewing the medical images rotate, tilt, and zoom, the tissue contained in the 3D cursor, it may be useful to see where the current viewpoint is relative to the initial viewpoint (e.g., voxels' locations have changed from initial orientation through rolling, pitching and/or yaw commands to a new orientation). This illustration shows a cured arrow originating at the initial viewing point and terminating at the current viewing point. Whether to display the icon or not would be under the control of the medical person viewing the medical images. The icon of a 3D cursor displays the contents of the 3D cursor which have been rotated and viewed from different viewpoints, it is useful to simultaneously see where the current position and view point are with respect to the original position.

Figure 22:
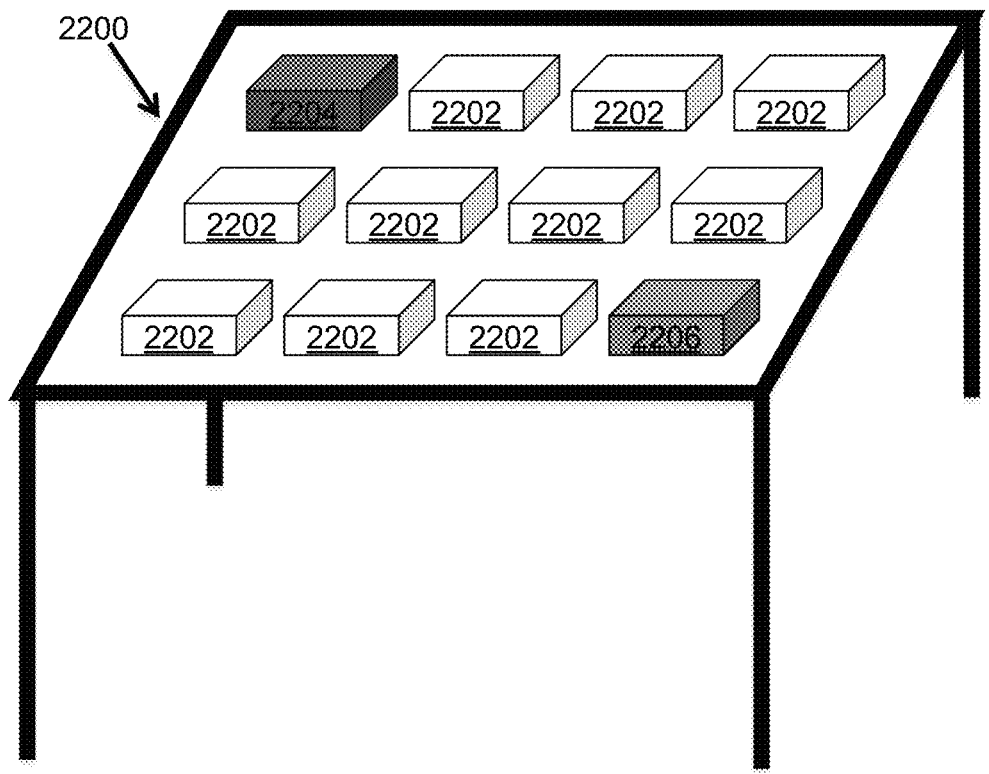
FIG. 22 illustrates a virtual moveable table for storing virtual images of suspect tissue stored by checklist category.

FIG. 22 illustrates a virtual moveable table for storing virtual images of suspect tissue stored by checklist category. This figure depicts a virtual movable table 2200 on which there are virtual storage bins that correspond to items on the medical institution checklist 2202, plus a bin for emergency items 2204, and a general/miscellaneous bin 2206 (e.g., image artifact, teaching case, quality improvement, etc.). The emergency bin 2204 could be used for placing findings for items of critical time sensitive information. The virtual mobile table is mobile in the sense that the user could view the virtual mobile table on an extended reality headset off to the side away from the imaging volume that the radiologist is currently working on. Then, the radiologist could move it or size it, such that it convenient for the work space. Items the medical personnel consider significant would be 'dragged and placed' in the respective virtual bins according to the checklist item being reviewed. For bins without significant items, there would be a statement 'unremarkable' on the checklist item on the report which goes away when an item is added, and the radiologist would replace that item on the checklist with the appropriate description. In addition to the reviewer, medical treatment personnel would be alerted and given access to the 'emergency bin' containing critical items. These items could be jointly reviewed by both treatment and review personnel on an expedited basis. This table with storage bins would facilitate the preparation of the report and enhance quality and completeness of the report. Current reporting is nominally limited to a word description only. Under this process, an annotated figure containing the tissue in question could be added.

FIG. 23 illustrates a sample radiology report including an image processed with virtual tools. Please note that the sample radiology report 2300 includes a 3D cursor and image finding of the abnormality.

What is claimed is:

1. A method comprising:
   selecting a three-dimensional image volume loaded in an image processing system;
   displaying said three-dimensional image volume on an extended reality head display unit;
   selecting a set of virtual tools from a group of available virtual tools responsive to user input;
   registering each virtual tool of the selected set with both the three-dimensional image volume and a corresponding tangible tool;
   manipulating the three-dimensional image volume in response to manipulation of ones of the set of virtual tools to generate a manipulated three-dimensional image volume
      wherein said manipulation of said ones of the set of virtual tools is performed by changing an orientation or a position of said corresponding tangible tool, and
      wherein said manipulation comprises altering said three-dimensional image volume's visual appearance; and
   displaying said manipulated three-dimensional image volume on said extended reality head display unit.

2. The method of claim 1 comprising selecting the set of virtual tools from a group of available virtual tools comprising: a virtual focal point pen; a virtual 3D cursor; a virtual transport viewer; a virtual pedestal; a virtual knife; a virtual catheter; a virtual road sign; a virtual ablation tool; a virtual table; a virtual contrast tool; and virtual icons.

3. The method of claim 1 wherein the set of virtual tools comprises a virtual focal point pen and comprising manipulating the three-dimensional image volume responsive to the virtual focal point pen by highlighting a portion of the three-dimensional image volume and adding annotations.

4. The method of claim 3 comprising altering a portion of the three-dimensional image volume adjacent to a tip of the virtual focal point pen.

5. The method of claim 1 wherein the set of virtual tools comprises a virtual knife and comprising manipulating the three-dimensional image volume responsive to the virtual knife consisting of at least one of the group consisting of separating portions of the three-dimensional image volume.

6. The method of claim 1 wherein the set of virtual tools comprises a virtual transport viewer and comprising:
   manipulating the three-dimensional image volume responsive to the virtual transport viewer by moving the virtual transport viewer within a hollow structure of the three-dimensional image volume and presenting an image from a perspective of the virtual transport viewer; and
   using the virtual transport viewer to perform a virtual colonoscopy.

7. The method of claim 1 wherein the set of virtual tools comprises a virtual contrast material and comprising:
   manipulating the three-dimensional image volume responsive to the virtual contrast material by inserting voxels into the three-dimensional image volume; and
   assigning data units values to different ones of the voxels.

8. The method of claim 1 wherein manipulating the three-dimensional image volume in response to manipulation of ones of the set of virtual tools comprises removing voxels of an outer shell of an organ in a repeated outer-shell by outer-shell fashion.

9. The method of claim 1 wherein manipulating the three-dimensional image volume in response to manipulation of ones of the set of virtual tools comprises spreading apart closely spaced tissue of interest by adjusting coordinates of voxels of the tissue of interest.

10. The method of claim 1 wherein the set of virtual tools comprises a virtual table and comprising manipulating the three-dimensional image volume responsive to the virtual table by placing portions of the three-dimensional image volume in a virtual storage bin of the virtual table.

11. The method of claim 1 wherein the set of virtual tools comprises a virtual catheter and comprising manipulating the three-dimensional image volume responsive to the virtual catheter by restricting movement of the virtual catheter to a column of blood voxels within a selected blood vessel.

12. The method of claim 1 comprising automatically displaying information associated with a selected sub-volume of the three-dimensional image volume wherein said information comprises patient's meta data and current condition for which obtaining the medical image volume was prompted, patient's medical history, laboratory results, and pathology results.

13. The method of claim 1 wherein the comprising displaying at least one of the group consisting of:
   an information on a virtual windshield;
   a distance with a virtual road sign;
   a visual aid icon indicating viewing perspective;
   each of sub-volume on a list of sub-volumes in a sequential fashion; and
   a visual aid icon indicating a finding detected by an artificial intelligence algorithm.

14. The method of claim 1 comprising selecting at least one of the group comprising:
   at least one sub-volume with a volume-subtending three-dimensional cursor;
   a sub-volume from a plurality of sub-volumes of a predetermined list of sub-volumes;
   a sub-volume from a plurality of sub-volumes defined by sequential search pattern coordinates; and
   a sub-volume from a plurality of sub-volumes defined by random search pattern coordinates.

15. The method of claim 1 wherein manipulating the three-dimensional image volume comprises at least one of: changing voxel size; changing voxel shape; changing voxel position; changing voxel orientation; changing voxel internal parameter; creating a voxel; eliminating a voxel; dividing a sub-volume volume of interest into multiple parts based on common characteristics; and, generating an exploded view wherein segmented structures of the three-dimensional image are moved away from a point in the three-dimensional image volume.

16. The method of claim 1 comprising employing a virtual eye tracker symbol to assist in human eye viewing.

17. The method of claim 16 comprising making the virtual eye tracker symbol appear and disappear at spatially separate lactations so that the human eye can perform saccades and jump from one location to another.

18. The method of claim 16 comprising making the virtual eye tracker symbol move smoothly along a path, so that the human eye can perform smooth tracking.

19. A non-transitory computer readable medium having computer readable code thereon for medical imaging, the medium comprising instructions for:
   selecting a three-dimensional image volume loaded in an image processing system;
   displaying said three-dimensional image volume on an extended reality head display unit;
   selecting a set of virtual tools from a group of available virtual tools responsive to user input;

registering each virtual tool of the selected set with both the three-dimensional image volume and a corresponding tangible tool;

manipulating the three-dimensional image volume in response to manipulation of ones of the set of virtual tools to generate a manipulated three-dimensional image volume
- wherein said manipulation of said ones of the set of virtual tools is performed by changing an orientation or a position of said corresponding tangible tool, and
- wherein said manipulation comprises altering said three-dimensional image volume's visual appearance; and displaying said manipulated three-dimensional image volume on said extended reality head display unit.

20. A computer system comprising:

a memory;

a processor; and wherein the memory is encoded with an application that when performed on the processor, provides a process for processing information, the process causing the computer system to perform the operations of:

selecting a three-dimensional image volume loaded in an image processing system;

displaying said three-dimensional image volume on an extended reality head display unit;

selecting a set of virtual tools from a group of available virtual tools responsive to user input;

registering each virtual tool of the selected set with both the three-dimensional image volume and a corresponding tangible tool;

manipulating the three-dimensional image volume in response to manipulation of ones of the set of virtual tools to generate a manipulated three-dimensional image volume
- wherein said manipulation of said ones of the set of virtual tools is performed by changing an orientation or a position of said corresponding tangible tool, and
- wherein said manipulation comprises altering said three-dimensional image volume's visual appearance; and displaying said manipulated three-dimensional image volume on said extended reality head display unit.

* * * * *